(12) United States Patent
Sher et al.

(10) Patent No.: US 9,051,331 B2
(45) Date of Patent: Jun. 9, 2015

(54) SUBSTITUTED DIHYDRO BENZOCYCLOALKYLOXYMETHYL OXAZOLOPYRIMIDINONES, PREPARATION AND USE THEREOF

(75) Inventors: Rosy Sher, Bridgewater, NJ (US); Raymond Walter Kosley, Jr., Bridgewater, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/410,723

(22) Filed: Mar. 2, 2012

(65) Prior Publication Data

US 2012/0184566 A1 Jul. 19, 2012

Related U.S. Application Data

(60) Provisional application No. PCT/US2010/048695, filed on Sep. 14, 2010, provisional application No. 61/242,586, filed on Sep. 15, 2009.

(30) Foreign Application Priority Data

Jul. 16, 2010 (FR) ...................................... 10 55806

(51) Int. Cl.
| | |
|---|---|
| *C07D 491/048* | (2006.01) |
| *C07D 498/04* | (2006.01) |
| *A61K 31/519* | (2006.01) |
| *A61K 31/522* | (2006.01) |

(52) U.S. Cl.
CPC ............ *C07D 498/04* (2013.01); *A61K 31/519* (2013.01); *A61K 31/522* (2013.01)

(58) Field of Classification Search
CPC ... A61K 31/519; A61K 31/522; C07D 498/04
USPC ...................................................... 514/259.2
See application file for complete search history.

(56) References Cited

U.S. PATENT DOCUMENTS

| | | | |
|---|---|---|---|
| 3,743,663 | A | 7/1973 | Baschang et al. |
| 5,641,785 | A | 6/1997 | Jegham et al. |
| 2005/0148590 | A1 | 7/2005 | Tsang et al. |
| 2006/0100460 | A1 | 5/2006 | Inoue et al. |
| 2010/0075994 | A1* | 3/2010 | Cao et al. .................. 514/259.2 |

FOREIGN PATENT DOCUMENTS

| | | |
|---|---|---|
| WO | WO 02/066484 | 8/2002 |
| WO | 2005/123738 | 12/2005 |
| WO | WO 2008/112483 A2 * | 3/2008 |
| WO | WO 2008/112483 | 9/2008 |

OTHER PUBLICATIONS

International Search Report for WO2011/034830 A1 dated Mar. 24, 2011.

Adetchessi et. al., Synthesis and Rearrangement of Cycloalkyl[1,2-e]Oxazolo[3,2-a]Pyrimidin-8/9-Ones: An Access to Cycloalkyl[1,2-d]Oxazolo[3,2-a]Pyrimidin-5-Ones, Tetrahedron, vol. 61, (2005), pp. 4453-4480.

Alexander, et. al , Metabotropic Glutamate Receptors as a Strategic Target for the Treatment of Epilepsy, Epilepsy Research, vol. 71, pp. 1-22. (2006).

Andrews, et al., Use of Methyllithium in Metal/Halogen Exchange: A Mild and Efficient Method for the Synthesis of Ortho Substitued Toluenes, Synthetic Communication, vol. 31, No. 15, pp. 2323-2327, (2001).

Baltzly, et al., The Addition of Secondary Amines to Some A-Benzai Ketones. Journal of the American Chemical Society, (1955), vol. 77, pp. 624-628.

Borsini, et. al., A Model to Measure Anticipatory Anxiety in Mice?, Psychopharmacology, (1989), vol. 98, pp. 207-211.

Cai, et. al., A Sequential Reaction Process to Assemble Polysubstituted Indolizidines, Quinolizidines and Quinolizidine Analogues. Tetrahedron, vol. 62, (2006), pp. 5697-5708.

Camps, et. al., Improved Synthesis of Methyl Alkoxyacetylenecarboxylates, Synthesis, (1989), pp. 123-124.

Carmen Carreno, et. al., Ring Selectivity in the Na/EtOH Reduction of 1-Aryl-7-Methoxynapthalenes. Synlett, (2005), vol. 10. pp. 1601-1605.

Chavez-Noriega, et. al., Metabotropic Glutamate Receptors: Potential Drug Targets for the Treatment of Schizophrenia. Current Drug Targets, • CNS & Neurological Disorders, (2002), vol. 1, pp. 261-281.

Feinberg, et. al., The Selective Group MgIu2/3 Receptor Agonist Ly379268 Suppresses Rem Sleep and Fast EEG in the Rat, Pharmacology, Biochemistry and Behavior, vol. 73, (2002), pp. 467-474.

(Continued)

*Primary Examiner* — Marcos Sznaidman
*Assistant Examiner* — Rayna B Rodriguez

(57) ABSTRACT

The present invention relates to a series of substituted dihydro benzocycloalkyl-oxymethyl oxazolopyrimidinones of formula (I):

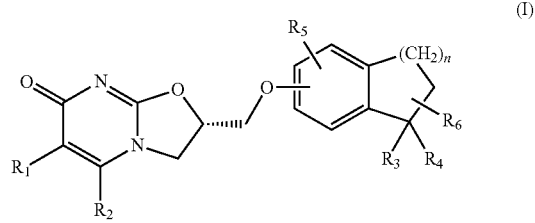

Wherein n, $R_1$, $R_2$, $R_3$, $R_4$, $R_5$ and $R_6$ are as defined herein. This invention also relates to methods of making these compounds including novel intermediates. The compounds of this invention are modulators of metabotropic glutamate receptors (mGluR), particularly, mGluR2 receptor. Therefore, the compounds of this invention are useful as pharmaceutical agents, especially in the treatment and/or prevention of a variety of central nervous system disorders (CNS), including but not limited to acute and chronic neurodegenerative conditions, psychoses, cognition deficit disorders, convulsions, anxiety, depression, migraine, pain, sleep disorders and emesis.

12 Claims, No Drawings

(56) References Cited

OTHER PUBLICATIONS

Forfar, et. al., An easy Route to 2-Substituted-2,3-Dihydro-5(7)H-Oxazolo[3,2-a]Pyrimidin-5-ones and 7-ones Starting from the Corresponding 2-Amino-2-Oxazolines, Journal of Heterocyclic Chemistry, (2001), vol. 38, No. 4, pp. 823-827.

Forfar, et. al., Synthesis, Structure, and Preliminary Pharmacological Evaluation of Cycloaddition Compounds with Unsaturated Carboxlic Esters, Archiv der Pharmazie, (1990), vol. 323, No. 11, pp. 905-909.

Galici, et. al., Biphenyl-Indanone A, A Positive Aliosteric Modulator of the Metabotropic Glutamate Receptor Subtype 2, Has Antipsychotic- and Anxiolytic-Like Effects in Mice, The Journal of Pharmacology and Experimental Therapeutics, (2006), vol. 318, No. 1, pp. 173-185.

Gewirtz, et. al., Modulation of DOI-Induced Increases in Cortical BDNF Expression by Group II mGlu Receptors, Pharmacology, Biochemistry and Behaviour, vol. 73, (2002), pp. 317-326.

Helton, et. al., Anxiolytic and Side-Effect Profile of Ly354740: A Potent, Highly Selective, Orally Active Agonist for Group II Metabotropic Glutamate Receptors, The Journal of Pharmacology and Experimental Therapeutics, vol. 284, No. 2, pp. 651-660. (1998).

Jirgensons, et. al., Synthesis and Structure-Affinity Relationships of 1,3,5-Alkylsubstituted Cyclohexylamines Binding at NMDA Receptor PCP Site, Eur. J. Med. Chem., vol. 35. (2000), pp. 555-565.

Johnson, et. al., Metabotropic glutamate 2 receptor potentiators: receptor modulation, frequency-dependent synaptic activity, and efficacy in preclinical anxiety and psychosis model(s), Psychopharmacology, (2005), vol. 179, pp. 271-283.

Jones, et. al., Analgesic Effects of the Selective Group II (mGlu2/3 Metabotropic Glutamate Receptor Agonists Ly379268 and Ly389795 in Persistent and Inflammatory Pain Models after Acute and Repeated Dosing, Neuropharmacology, vol. 49, (2005), pp. 206-218.

Kawashima, et. al., Neuropharmacological Profiles of Antagonists of Group II Metabotropic Glutamate Receptors, Nueroscience Letters, vol. 378, (2005), pp. 131-134.

Kellner, et al., Effects of a metabotropic glutamate2/3 receptor agonist (LY544344/LY354740) on panic anxiety induced by cholecystokinin tetrapeptide in healthy humans: preliminary results, Psychopharmacology (2005) 179 pp. 310-315.

Kimaru, et. al., Silver(I)-Catalyzed Aminocyclization of 2,3-Butadienyl and 3,4-Pentadienyl Carbamates: An Efficient and Stereoselective Synthesis of 4-Vinyl-2-Oxazolidinones and 4-Vinyltetrahydro-2H-1,3-Oxacin-2-Ones, Bull. Chem. Soc. Jpn., vol. 68, pp. 1689-1705, (1995).

Konishi, et. al., A Mild Selective Monobromination Reagent System for Alkoxybenzenes; N-Bromosuccinimide-Silica Gel, Bull. Chem. Soc. Jpn, vol. 62, pp. 591-593, (1989).

Krystal, et al., Preliminary Evidence of Attenuation of the Disruptive Effects of the NMDA Glutamate Receptor Antagonist, Ketamine, on Working Memory by Pretreatment With the Group II Metabotropic Glutamate Receptor Agonist, LY354740, in Healthy Human Subjects. Psychopharmacology, vol. 179, pp. 303-309, (2005).

Lee, et al., The Effect of MGlur2 Activation on Signal Transduction Pathways and Neurorial Cell Survival, Brain Research, vol. 1249, vol. 1249, (2009), pp. 244-250.

Lissavetzky. et al , Synthesis of 4-Substituted Methyl 3-(2,3-Epoxy) Propoxythiophene-2-Carboxylates, Heterocycles, vol. 43, No. 4, (1996), pp. 775-780.

Martinez, et. al.. A New and Convenient Synthesis of Alkyl and Aryl Pyrimidines. J. Heterocyclic Chem., vol. 25, pp. 1237-1241, (1988).

Moghaddam, et al., Targeting Metabotropic Glutamate Receptors For Treatment of the Cognitive Symptoms of Schizophrenia, Psychopharmacology, vol. 174, pp. 39-44, (2004).

Monaghan, et. al., The Excitatory Amino Acid Receptors: Their Classes, Pharmacology, and Distinct Properties in the Function of the Central Nervous System, Annu. Rev, Pharmacol. Toxicol., (1989), vol. 29, pp. 365-402.

Olivier, et. al., Stress-Induced Hyperthermia and Anxiety: Pharmacological Validation, European Journal of Pharmacology, vol. 452, (2003), pp. 117-132.

Patil, et. al., Activation of MGlu2/3 Receptors as a New Approach to Treat Schizophrenia: A Randomized Phase 2 Clinical Trial, Nature Medicine, vol. 13, No. 9, (2007), pp. 1102-1107.

Poulter. Synthesis of Fluorinated Analogues of Geraniol, J. Org. Chem.. (1981), vol. 46, pp. 1532-1538.

Rorick-Kehn, et. al., Improved Bioavailability of the MGlu2/3 Receptor Agonist Ly354740 Using a Prodrug Strategy: In Vivo Pharmacology of Ly54434, The Journal of Pharmacology and Experimental Therapeutics, (2006), vol. 316, No. 2, pp. 905-913.

Sabbatini, et. al., Metabotropic Glutamate Receptors. Potential Therapeutic Applications of Recently Disclosed New Chemical Entities, Expert Opin. Ther. Patent, (2004), vol. 14, No. 11, pp. 1593-1604.

Samadi, et al., Basal Ganglia Group II Metabotropic Glutamate Receptors Specific Binding in Non-Human Primate Model of L-Dopa-Induced Dyskinesias, Neuropharmacology, vol. 54, (2008), pp. 258-268.

Schechter, et. al., Innovative Approaches for the Development of Antidepressant Drugs: Current and Future Strategies. NeuroRx. The Journal of the American Society for Experimental NeuroTherapeutics, vol. 2, pp. 590-611. (2005).

Tartarczynska et al., The Antianxiety-Like Effects of Antagonists of Group 1 and Agonists of Group II and III Metabotropic Glutamate Receptors After Intrahippocampal Administration, Psychopharmacology, (2001) vol. 158, No. 1, pp. 94-99.

Thomsen, et. al., (S)-4-Carboxy-3-Hydroxyphenylglycine, An Antagonist of Metabotropic Glutamate Receptor (MGlur)1a and an Agonist of MGluR2, Protects Against Audiogenic Seizures in DBA/2 Mice, Journal of Neurochemistry, vol. 62, No. 6, pp. 2492-2495. (1994).

Thomsen, et. al., Roles of Metabotropic Glutamate Receptor Subtypes in Modulation of Pentylenetetrazole-Induced Seizure Activity in Mice, Neuropharmacology, vol. 37, (1998), pp. 1465-1473.

Urgaonkar, et. al., Palladium/Proazaphosphatrane-Catalyzed Amination of Aryl Halides Possessing a Phenol, Alcohol, Acetanilide, Amide of an Enolizable Ketone Functional Group: Efficacy of Lithium Bis (Trimethylsilyl)Amide as the Base, Adv. Synth. Catal., (2004), vol. 346, pp. 611-616.

Watkins, et al., Structure-activity relationships in the development of excitatory amino acid receptor agonists and competitive antagonists, Trends in Pharma. Sci. (1990) 11 pp. 25-33.

Watkins, et. al., Excitatory Amino Acid Transmitters, Ann. Rev Pharmacol. Toxicol , (1981), vol. 21, pp. 185-204.

Yang, et. al., Gold(I)-Catalyzed Intermolecular Additions of Phenols and Carboxylic Acids to Olefins, J. Am. Chem. Soc.. (2005), vol. 127, pp. 6966-6967.

Yeager, et. al , A Convenient Method for the Preparation of 4-Aryloxyphenols, Synthesis, (1991), pp. 63-68.

Zhang, et. al., Synthesis of beta- and gamma-Carbolines by the Paladium-Catalyzed Iminoannulation of Alkynes. J. Org. Chem.. (2002), vol. 67. pp. 9318-9330.

Klodzinska, et al., Selective Group II Glutamate Metabotropic Receptor Agonist LY354740 Attenuates Pentetrazole- and Picrotoxin-Induced Seizures, Pol. J. Pharmacol., (1999), vol. 51, pp. 543-645.

Bradley, et al., Activation of Group II Metabotropic Glutamate Receptors Inhibits Synaptic Excitation of the Substantia Nigra Pars Reticulata. The Journal of Neuroscience, (2000), vol. 20, No. 9, pp. 3085-3094.

Conn, et al., Activation of Metabotropic Glutamate Receptors as a Novel Approach for the Treatment of Schizophrenia, Trends in Pharmacological Sciences. vol. 30, No. 1, pp. 25-31. (2008).

(56) References Cited

OTHER PUBLICATIONS

Krystal, et al., NMDA Receptor Antagonist Effects, Cortical Glutamatergic Function, and Schizophrenia: Toward a Paradigm Shift in Medication Development, Psychopharmacology, (2003), vol. 169, pp. 215-233.

Lorrain, et al., Effects of Ketamine and N-Methyl-D-Aspartate on Glutamate and Dopamine Release in the Rat Prefrontal Cortex: Modulation by a Group II Selective Metabotropic Glutamate Receptor Agonist Ly379268, Neuroscience, vol. 117, (2003). pp. 697-706.

Rouse, et al., Distribution and Roles of Metabotropic Gluatamate Receptors in the Basal Ganglia Motor Circuit Implications for Treatment of Parkinson's Disease and Related Disorders, Pharmacology & Therapeutics, vol. 88, (2000), pp. 427-435.

U.S. Appl. No. 12/554,129—Non Final Office Action dated Nov. 6, 2012.

U.S. Appl. No. 12/554,129—Non Final Office Action dated May 29, 2012.

* cited by examiner

SUBSTITUTED DIHYDRO BENZOCYCLOALKYLOXYMETHYL OXAZOLOPYRIMIDINONES, PREPARATION AND USE THEREOF

BACKGROUND OF THE INVENTION

1. Field of the Invention

The present invention relates to a series of substituted dihydro benzocycloalkyloxymethyl oxazolopyrimidinones. More specifically, the present invention relates to a series of substituted 2-benzocycloalkyloxymethyl-2,3-dihydro-oxazolo[3,2-a]pyrimidin-7-ones. This invention also relates to methods of making these compounds. The compounds of this invention are allosteric modulators of metabotropic glutamate receptors (mGluR), particularly, mGluR2. Therefore, the compounds of this invention are useful as pharmaceutical agents, especially in the treatment and/or prevention of a variety of diseases including diseases associated with the central nervous system.

2. Description of the Art

Recently, there has been a considerable amount of research involving L-glutamate, which is the most abundant neurotransmitter in the central nervous system (CNS). More specifically, L-glutamate mediates the major excitatory pathways in mammals, and is therefore referred to as an excitatory amino acid (EAA). Thus the receptors that respond to glutamate are known as excitatory amino acid receptors (EAA receptors). Based on the extensive research performed lately it can be readily discerned that EAAs are of great physiological importance. Particularly, EAAs are known to play a role in several physiological processes including long-term potentiation (learning and memory), the development of synaptic plasticity, motor control, respiration, cardiovascular regulation and sensory perception, just to name a few. See, e.g., Watkins & Evans, Annual Reviews in Pharmacology and Toxicology, 21:165 (1981); Monaghan, Bridges, and Coltman, Annual Reviews in Pharmacology and Toxicology, 29:365 (1989); Watkins, Krogsgaard-Larsen and Honore, Transactions in Pharmaceutical Science, 11:25 (1990).

Broadly, the EAA receptors are classified into two types: 1) "ionotropic"—which are directly coupled to the opening of cation channels in the cell membrane of the neurons; and 2) "metabotropic"—which are G-protein coupled receptors (GPCR). The excessive or inappropriate stimulation of EAA receptors leads to neuronal cell damage or loss by way of a mechanism known as excitotoxicity. This process has been suggested to mediate neuronal degeneration in a variety of conditions. Thus there is a renewed interest in developing small molecule new drugs to alleviate these conditions.

The metabotropic glutamate receptors (mGluR) are a highly heterogeneous family of glutamate receptors that are linked to multiple second-messenger pathways. One function of these receptors is to modulate the presynaptic release of glutamate and the postsynaptic sensitivity of the neuronal cell to glutamate excitation. Thus it has been reported widely in the literature that agonists and antagonists of these receptors are useful in the treatment of a variety of disease conditions including acute and chronic neurodegenerative conditions, psychoses, convulsions, anxiety, depression, migraine, pain, sleep disorders and emesis.

The metabotropic glutamate receptors (mGluR) are again classified into three groups based on receptor homology and signaling mechanisms. Among them, recent pharmacological and histochemical studies have suggested that the group II mGluR (mGluR2 and mGluR3) plays crucial roles in the control of emotional states. For example, MGS0039, a selective group II mGluR antagonist, has been shown to exhibit dose-dependent antidepressant-like effects in some animal models. See, e.g., Kawashima, et al., Neurosci. Lett., 2005, 378(3):131-4.

Recently, it has also been reported that glutamate/N-methyl-D-aspartate glutamate receptors (NMDAR) are implicated in schizophrenia. This was indeed supported by the observation that administration of NMDAR blockers to human volunteers is psychotomimetic and administration to schizophrenia patients exacerbates pre-existing symptoms. For example, systemic administration of group II mGluR agonists suppress phencyclidine (PCP) induced behavioral effects and the increase in glutamate efflux. It has also been observed that activation of group II mGluRs (mGluR2 and mGluR3) decreases glutamate release from presynaptic nerve terminals, suggesting that group II mGluR agonists may be beneficial in the treatment of schizophrenia. See, e.g., Chavez-Noriega et al., Current Drug Targets—CNS & Neurological Disorders, 2002, 1, 261-281.

Although there is a great deal of interest in developing small molecule drugs that are active at the mGluR sites, the researchers are faced with a lack of potent and selective molecules. In spite of this, there are innumerable reports highlighting the great interest around these potential therapeutic targets. See, e.g., Sabbatini and Micheli, Expert Opin. Ther. Patents (2004) 14(11):1593-1604.

However, there is still a need to develop selective compounds for one subtype over another metabotropic glutamate receptor site. One strategy that has recently emerged involves the discovery of allosteric modulators that do not bind at the glutamate binding site. An allosteric modulator only works if the agonist (glutamate) is present at the orthosteric binding site; thus, an allosteric modulator will only potentiate or block effects produced by the presence of an agonist, but have no activity on its own. Such a strategy is believed to confer greater specificity to desired pharmacological effects because they affect the normal physiological activity of the agonist.

In addition, there is still a considerable interest in developing small molecule "drug like" compounds that exhibit improved potency and modulation of mGluR2 as well as improved brain penetration. There is also an interest in developing modulators of mGluR2 that are devoid of typical side effects exhibited by typical and atypical antipsychotic compounds, such as for example extrapyramidal symptoms including tardive dyskinesia, weight gain, etc. It is also expected that allosteric modulators that exhibit improved subtype selectivity will feature an improved pharmacological safety profile. It is further believed that a selective modulator of mGluR2 will also exhibit efficacy on cognitive dysfunction in schizophrenia patients thereby improving working memory and positive symptoms.

WO2008/112483 discloses a series of 2-substituted-2,3-dihydro-oxazolo[3,2-a]pyrimidin-7-ones and 2-substituted-2,3,5,6-tetra-hydro-oxazolo[3,2-a]pyrimidin-7-ones, which are allosteric modulators of metabotropic glutamate receptors (mGluR), particularly, mGluR2.

In addition to exhibiting required allosteric modulation properties the intended drug substance must also meet various "drug-like" properties including but not limited to good adsorption, distribution, metabolism and excretion (ADME) properties as well as pharmacokinetics. For instance, in order for the drug substance to be effective it must interact suitably with various enzymes produced in the body, including cytochrome P450 enzyme or CYPs, esterases, proteases, reductases, dehydrogenases, and the like. Generally it is necessary that the compounds that are suitable as "drugs" must have good CYP-isozyme interaction properties. More notably, it has been observed generally that compounds exhibiting minimal CYP induction and optimal CYP contribution are considered to possess favorable "drug like" properties among other desirable properties. Specific CYP isozymes include CYP3A4, CYP2D6, CYP2C9, among others.

Accordingly, the compounds of the instant invention, notably, substituted 2-benzocycloalkyloxymethyl-2,3-dihydrooxazolo[3,2-a]pyrimidin-7-ones are found to be not only effective potentiators of mGluR2 but also exhibit improved "drug-like" properties as described herein.

SUMMARY OF THE INVENTION

Thus in accordance of this invention there are provided compounds of the formula I:

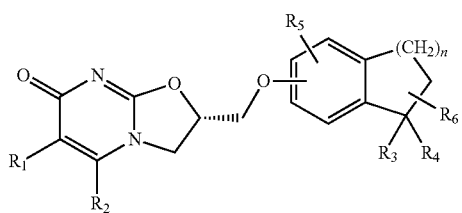

(I)

wherein:

n is 1, 2 or 3;

$R_1$ is selected from the group consisting of hydrogen, methyl, fluoromethyl, ethyl, 2-fluoroethyl and propyl;

$R_2$ is selected from the group consisting of hydrogen, methyl, fluoromethyl, ethyl, 2-fluoroethyl, propyl, 1,1-difluoropropyl, methoxymethyl, 2-fluoroethoxymethyl and ethoxy-1-fluoroethyl;

$R_3$ and $R_4$ are the same or different and independently of each other selected from the group consisting of $(C_1-C_4)$ alkyl, phenyl and benzyl; or $R_3$ and $R_4$ taken together with the carbon atom to which they are attached form a substituted or unsubstituted $C_3-C_7$ carbocyclic ring; and $R_5$ and $R_6$ are the same or different and independently of each other selected from the group consisting of hydrogen, halogen, $(C_1-C_4)$alkyl and $(C_1-C_4)$alkoxy.

In addition, various embodiments of this invention including pharmaceutical compositions comprising various compounds of this invention as well as their use in the treatment of a variety of disorders and/or disease conditions as disclosed herein are also part of this invention all of which are described in detail below.

DETAILED DESCRIPTION OF THE INVENTION

The terms as used herein have the following meanings:

As used herein, the expression "$(C_1-C_4)$alkyl" includes methyl and ethyl groups, and straight-chain or branched propyl and butyl groups. Particular alkyl groups are methyl, ethyl, n-propyl, isopropyl and tert-butyl. It should particularly be noted that any of the feasible branched $(C_1-C_4)$alkyl group known in the art is encompassed by this expression. Derived expressions such as "$(C_1-C_4)$alkoxy", "$(C_1-C_4)$thioalkyl", "$(C_1-C_4)$alkoxy$(C_1-C_4)$alkyl" or "hydroxy$(C_1-C_4)$alkyl", "$(C_1-C_4)$alkylcarbonyl", "$(C_1-C_4)$alkoxycarbonyl$(C_1-C_4)$alkyl", "$(C_1-C_4)$alkoxycarbonyl", "amino$(C_1-C_4)$alkyl", "$(C_1-C_4)$alkylamino", "$(C_1-C_4)$alkylcarbamoyl$(C_1-C_6)$alkyl", "$(C_1-C_4)$dialkylcarbamoyl$(C_1-C_4)$alkyl" "mono- or di-$(C_1-C_4)$alkylamino$(C_1-C_4)$alkyl", "amino$(C_1-C_4)$alkylcarbonyl" "diphenyl$(C_1-C_4)$alkyl", "phenyl$(C_1-C_4)$alkyl", "phenylcarboyl$(C_1-C_4)$alkyl", "phenoxy$(C_1-C_4)$alkyl" and "$(C_1-C_4)$alkylsulfonyl," are to be construed accordingly. Similarly other derived expressions, such as $(C_1-C_4)$alkoxyethoxy shall be construed accordingly. Another derived expression mono- or di-fluoro$(C_1-C_4)$alkyl shall mean that one or two of the hydrogens are replaced with fluorine. Representative examples of monofluoro$(C_1-C_4)$alkyl include fluoromethyl, 2-fluoro-eth-1-yl or 1-fluoro-eth-1-yl, 1-fluoro-1-methyl-eth-1-yl, 2-fluoro-1-methyl-eth-1-yl, 3-fluoro-prop-1-yl, and the like. Representative examples of difluoro$(C_1-C_4)$alkyl include difluoromethyl, 2,2-difluoro-eth-1-yl, 1,2-difluoro-eth-1-yl or 1,1-difluoro-eth-1-yl, 1,2-difluoro-1-methyl-eth-1-yl, 2,2-difluoro-1-methyl-eth-1-yl, 1,3-difluoro-prop-1-yl, and the like.

As used herein, the expression "$(C_3-C_7)$cycloalkyl" or "$(C_3-C_7)$carbocyclic ring" includes all of the known cyclic radicals. Representative examples of "cycloalkyl" or "carbocyclic" includes without any limitation cyclopropyl, cyclobutyl, cyclopentyl, cyclohexyl, cycloheptyl, and the like. Derived expressions such as "cycloalkoxy" or "cycloalkyloxy", "cycloalkyloxyethoxy", "cycloalkylalkyl", "cycloalkylaryl", "cycloalkylcarbonyl" are to be construed accordingly. It should further be noted that the expression "$(C_5-C_8)$carbocyclic" shall have the same meaning as "$(C_5-C_8)$cycloalkyl".

"Halogen" (or "halo") means chlorine (chloro), fluorine (fluoro), bromine (bromo), and iodine (iodo).

As used herein, "patient" means a warm blooded animal, such as for example rats, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

As used herein, the term "prodrug" shall have the generally accepted meaning in the art. One such definition includes a pharmacologically inactive chemical entity that when metabolized or chemically transformed by a biological system such as a mammalian system is converted into a pharmacologically active substance.

The expression "stereoisomers" is a general term used for all isomers of the individual molecules that differ only in the orientation of their atoms in space. Typically it includes mirror image isomers that are usually formed due to at least one asymmetric center (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

The term "solvate" as used herein means that an aggregate that consists of a solute ion or molecule with one or more solvent molecules. Similarly, a "hydrate" means that a solute ion or molecule with one or more water molecules.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_{20})$alkyl, $(C_2-C_6)$alkenyl, $(C_1-C_6)$perfluoroalkyl, phenyl, hydroxy, —$CO_2H$, an ester, an amide, $(C_1-C_6)$alkoxy, $(C_1-C_6)$thioalkyl, $(C_1-C_6)$perfluoroalkoxy, —$NH_2$, Cl, Br, I, F, CN, $SF_5$, —NH-lower alkyl, and —N(lower alkyl)$_2$, unless otherwise noted. However, any of the other suitable substituents known to one skilled in the art can also be used in these embodiments.

"Therapeutically effective amount" means an amount of the compound which is effective in treating the named disease, disorder or condition.

The term "treating" refers to:
(i) preventing a disease, disorder or condition from occurring in a patient that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Thus, in accordance with the practice of this invention there is provided a compound of the formula I:

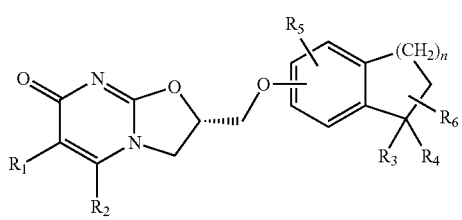

(I)

wherein:
n is 1, 2 or 3;
$R_1$ is selected from the group consisting of hydrogen, methyl, fluoromethyl, ethyl, 2-fluoroethyl and propyl;
$R_2$ is selected from the group consisting of hydrogen, methyl, fluoromethyl, ethyl, 2-fluoroethyl, propyl, 1,1-difluoropropyl, methoxymethyl, 2-fluoroethoxymethyl and ethoxy-1-fluoroethyl;
$R_3$ and $R_4$ are the same or different and independently of each other selected from the group consisting of $(C_1-C_4)$alkyl, phenyl and benzyl; or
$R_3$ and $R_4$ taken together with the carbon atom to which they are attached form a substituted or unsubstituted $C_3-C_7$ carbocyclic ring; and
$R_5$ and $R_6$ are the same or different and independently of each other selected from the group consisting of hydrogen, halogen, $(C_1-C_4)$alkyl and $(C_1-C_4)$alkoxy.

As already mentioned above, the compound of formula I may be present as a salt when such possibility exists. All forms of salts that can be envisaged are part of this invention.

In an embodiment of this invention the compound of this invention is represented by formula (II):

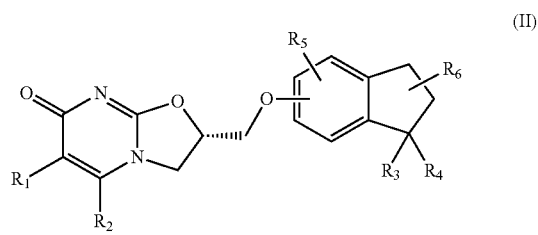

(II)

wherein:
$R_1$ is selected from the group consisting of hydrogen, methyl and ethyl;
$R_2$ is selected from the group consisting of hydrogen, methyl, ethyl, propyl and 1,1-difluoropropyl;
$R_3$ and $R_4$ are the same or different and independently of each other selected from the group consisting of methyl, ethyl and propyl; or
$R_3$ and $R_4$ taken together with the carbon atom to which they are attached form cyclopropyl, cyclobutyl or cyclopentyl ring; and
$R_5$ and $R_6$ are the same or different and independently of each other selected from the group consisting of hydrogen, fluorine, chlorine, bromine, methyl and ethyl.

In another embodiment of this invention the compound of formula (II) is having the following substituents:
$R_1$ is hydrogen or ethyl;
$R_2$ is hydrogen or methyl;
$R_3$ and $R_4$ are each methyl; and
$R_5$ is hydrogen, fluorine or methyl;
$R_6$ is hydrogen or methyl.

As specific examples of compound of formula (II), the following compounds may be enumerated without any limitations:
(S)-2-(1,1-dimethyl-indan-5-yloxymethyl)-2,3-dihydro-oxazolo[3,2-a]pyrimidin-7-one;
(S)-2-(6-bromo-1,1-dimethyl-indan-5-yloxymethyl)-2,3-dihydro-oxazolo[3,2-a]pyrimidin-7-one;
(S)-2-(6-chloro-1,1-dimethyl-indan-5-yloxymethyl)-2,3-dihydro-oxazolo[3,2-a]pyrimidin-7-one;
(S)-2-(6-fluoro-1,1-dimethyl-indan-5-yloxymethyl)-2,3-dihydro-oxazolo[3,2-a]pyrimidin-7-one;
(S)-2-(1,1,6-trimethyl-indan-5-yloxymethyl)-2,3-dihydro-oxazolo[3,2-a]pyrimidin-7-one;
(S)-2-(1,1-dimethyl-indan-5-yloxymethyl)-6-ethyl-2,3-dihydro-oxazolo[3,2-a]pyrimidin-7-one;

(S)-5-(1,1-difluoro-propyl)-2-(1,1-dimethyl-indan-5-yloxymethyl)-2,3-dihydro-oxazolo[3,2-a]pyrimidin-7-one; and (S)-2-(1,1-dimethyl-indan-5-yloxymethyl)-5-methyl-2,3-dihydro-oxazolo[3,2-a]pyrimidin-7-one.

More specifically, the following compounds are enumerated as compounds of formula (II):

(S)-2-(6-fluoro-1,1-dimethyl-indan-5-yloxymethyl)-2,3-dihydro-oxazolo[3,2-a]pyrimidin-7-one;

(S)-2-(6-bromo-1,1-dimethyl-indan-5-yloxymethyl)-2,3-dihydro-oxazolo[3,2-a]pyrimidin-7-one;

(S)-2-(1,1,6-trimethyl-indan-5-yloxymethyl)-2,3-dihydro-oxazolo[3,2-a]pyrimidin-7-one; and (S)-2-(6-chloro-1,1-dimethyl-indan-5-yloxymethyl)-2,3-dihydro-oxazolo[3,2-a]pyrimidin-7-one.

In another embodiment, the compound of this invention can be represented by formula

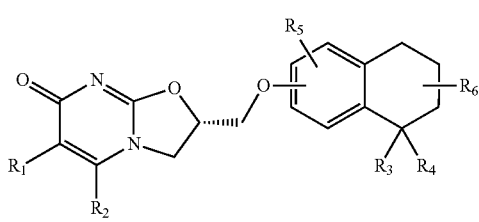

(III)

wherein:
$R_1$ is selected from the group consisting of hydrogen, methyl and ethyl;
$R_2$ is selected from the group consisting of hydrogen, methyl, ethyl, propyl and 1,1-difluoropropyl;
$R_3$ and $R_4$ are the same or different and independently of each other selected from the group consisting of methyl, ethyl and propyl; or
$R_3$ and $R_4$ taken together with the carbon atom to which they are attached form cyclopropyl, cyclobutyl or cyclopentyl ring; and
$R_5$ and $R_6$ are the same or different and independently of each other selected from the group consisting of hydrogen, fluorine, chlorine, bromine, methyl and ethyl.

The compound of formula (III) can also present in the form of a salt; all such forms are part of this invention.

In an embodiment of this invention the compound of formula (III) is having:
$R_1$ is hydrogen or ethyl;
$R_2$ is hydrogen, methyl or 1,1-difluoropropyl;
$R_3$ and $R_4$ are each methyl; and
$R_5$ is hydrogen, fluorine or methyl;
$R_6$ is hydrogen or methyl.

As specific examples of the compound of formula (III) without any limitation, the following compounds are enumerated:

(S)-2-(5,5-dimethyl-5,6,7,8-tetrahydro-naphthalen-2-yloxymethyl)-2,3-dihydro-oxazolo[3,2-a]pyrimidin-7-one;

(S)-2-(5,5-dimethyl-5,6,7,8-tetrahydro-naphthalen-2-yloxymethyl)-6-ethyl-2,3-dihydro-oxazolo[3,2-a]pyrimidin-7-one (S)-2-(5,5,8,8-tetramethyl-5,6,7,8-tetrahydro-naphthalen-2-yloxymethyl)-2,3-dihydro-oxazolo[3,2-a]pyrimidin-7-one; and (S)-5-(1,1-difluoro-propyl)-2-(5,5-dimethyl-5,6,7,8-tetrahydro-naphthalen-2-yloxymethyl)-2,3-dihydro-oxazolo[3,2-a]pyrimidin-7-one.

In another embodiment of this invention, the compound of this invention can be represented by formula IV:

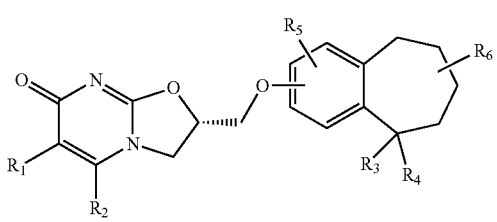

(IV)

wherein:
$R_1$ is selected from the group consisting of hydrogen, methyl and ethyl;
$R_2$ is selected from the group consisting of hydrogen, methyl, ethyl, propyl and 1,1-difluoropropyl;
$R_3$ and $R_4$ are the same or different and independently of each other selected from the group consisting of methyl, ethyl and propyl; or
$R_3$ and $R_4$ taken together with the carbon atom to which they are attached form cyclopropyl, cyclobutyl or cyclopentyl ring; and
$R_5$ and $R_6$ are the same or different and independently of each other selected from the group consisting of hydrogen, fluorine, chlorine, bromine, methyl and ethyl.

The compound of formula (IV) can also present in the form of a salt; all such forms are part of this invention.

In a further embodiment of this invention, the compound of formula (IV) is having:
$R_1$ is hydrogen;
$R_2$ is hydrogen;
$R_3$ and $R_4$ are each methyl; and
$R_5$ is hydrogen, fluorine or methyl;
$R_6$ is hydrogen or methyl;
or a salt thereof.

As a specific example of the compound of formula (IV) without any limitation, the following compound is enumerated:

(S)-2-(5,5-dimethyl-6,7,8,9-tetrahydro-5H-benzocyclohepten-2-yloxymethyl)-2,3-dihydro-oxazolo[3,2-a]pyrimidin-7-one.

The above compound can present in the form of a salt.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein.

More specifically, the compounds disclosed herein can be synthesized according to the following procedures of Schemes 1-8, wherein the n, $R_1$, $R_2$, $R_3$, $R_4$, $R_5$ and $R_6$, are as defined for Formula I unless otherwise indicated.

Scheme 1 illustrates the synthesis of several of the compounds of formula (I) of this invention wherein $R_1$, $R_5$ and $R_6$ are hydrogen. However, a similar synthetic scheme can be adopted for other compounds of formula (I) of this invention wherein $R_1$, $R_5$ and $R_6$ are other than hydrogen as defined herein.

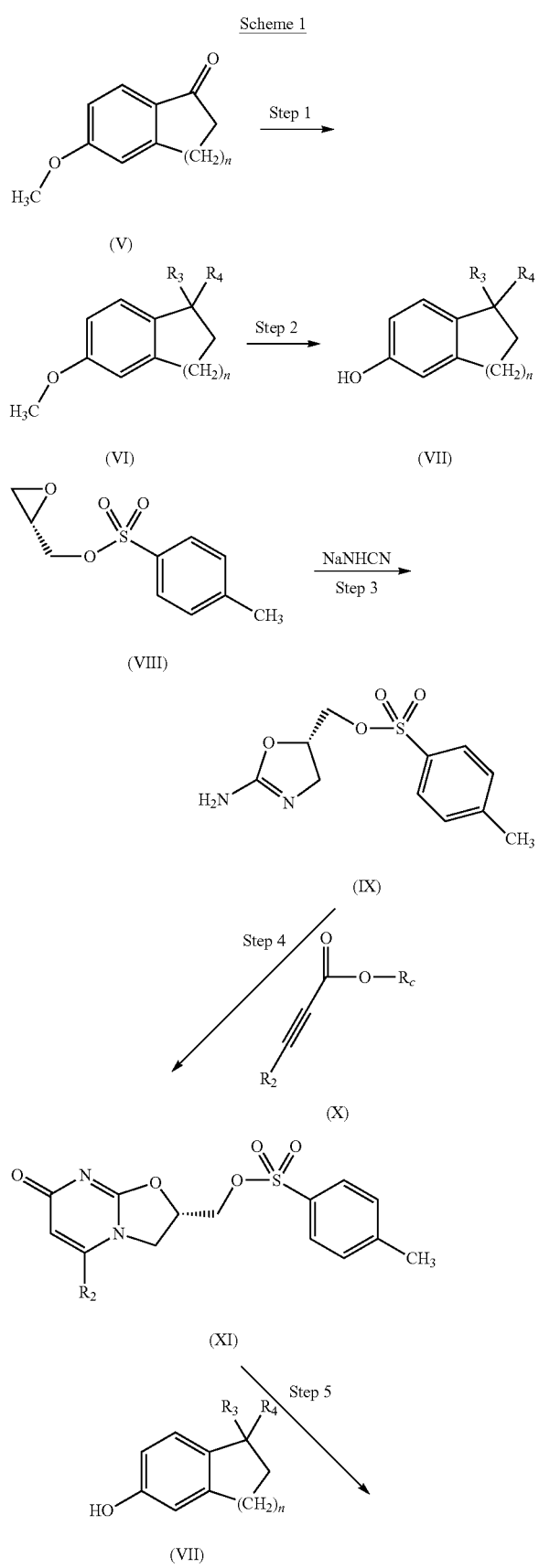

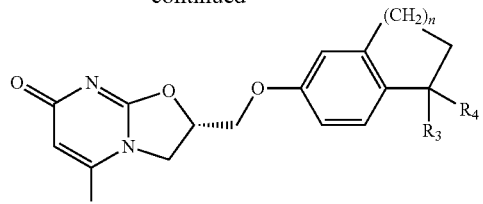

In Step 1, Scheme 1, methoxy-benzocycloalkanone of formula V is reacted with suitable reagent to form a compound of formula (VI). In general such reactions can be affected by a dialkyl or diaryl metal reagent of formula $MR_3R_4$. For instance, zinc reagent can be employed. More specifically, such reactions are disclosed in U.S. Pat. Appl. Publ. 2006100460.

In Step 2, Scheme 1, the compound of formula (VI) is further demethylated to form compound of formula (VII). Any of the known procedures which bring about such demethylation can be employed herein. Examples of such reactions include without any limitation cleavage of methoxy groups by Lewis acids such as boron tribromide or using iodotrimethylsilane reagent or any other equivalent reagents.

In Step 3, Scheme 1, (S)-glycidyltosylate of formula (VIII) is reacted with a suitable cyanamide compound to form an oxazolylamine of formula (IX) in a suitable solvent. Any of the known cyanamide compounds that react with an epoxide to form oxazolylamines can be employed in this reaction. Suitable cyanamides for this purpose include without any limitation, sodium hydrogen cyanamide, lithium hydrogen cyanamide, potassium hydrogen cyanamide, cesium hydrogen cyanamide, and the like. For instance, Scheme 1 exemplifies sodium hydrogen cyanamide as a suitable cyanamide compound. The reaction can generally be carried out in alcoholic solvents such as methanol, ethanol, isopropanol and the like or a mixture thereof. The reaction is further carrier out at a suitable temperature, for example, at about ambient to super-ambient temperatures.

In Step 4, Scheme 1, the oxazolylamine of formula (IX) is reacted with an α,β-unsaturated alkynoic ester of formula (X), wherein $R_c$ is ($C_1$-$C_4$)alkyl, phenyl or benzyl, to form the compound of formula (XI). This reaction can again be carried out using any of the procedures known to one skilled in the art. Typically, such an addition reaction is carried out in a suitable alcoholic solvent such as methanol, ethanol or isopropanol or a mixture thereof. Such addition reactions can also be carried out using α,β-unsaturated alkynoic ester of formula (X) itself as the solvent. The reaction is generally carried out at ambient to super-ambient temperature conditions. More generally, the reaction is carried out at the reflux temperature of the solvent. However, super-ambient temperatures involving the microwave oven can also be employed to carry out this reaction at a temperature ranging from about 100° C. to about 200° C.

In Step 5, Scheme 1, the compound of formula (XI) obtained in Step 4 is reacted with a compound of formula (VII) obtained in Step 2. Such substitution reactions are generally carried out in an aprotic polar solvent, such as DMF or acetonitrile and in the presence of a suitable base such as alkali carbonates for example cesium carbonate or an organic base such as triethylamine. Alternatively a compound of formula (XI) in an aprotic solvent such as DMF or acetonitrile/ dichloromethane/DMSO can be treated with a mixture of sodium hydride and compound of formula (VII) in a suitable solvent such as acetonitrile or DMF. The reaction temperatures can be sub-ambient to ambient to super-ambient, but typically the reaction is carried out under ambient to moderately higher temperatures in the range of 30 to 60° C. Various other compounds of formula (I) can similarly be prepared using appropriate starting materials.

Scheme 2 illustrates another approach for the preparation of compounds of this invention wherein $R_2$ is hydrogen and $R_1$ is as defined herein. However, variations of this schematic approach can be used for preparing other variants of the compound of formula (I) wherein $R_2$ is other than hydrogen.

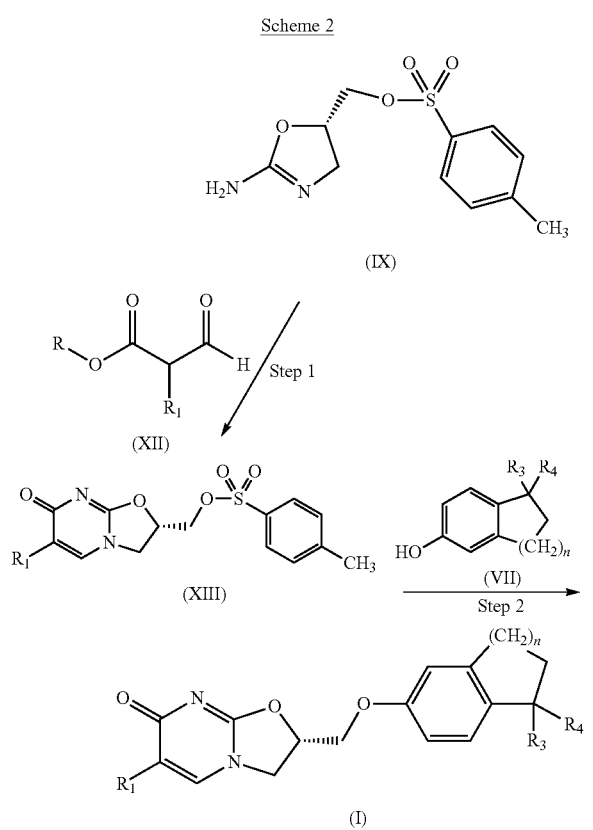

In Step 1, Scheme 2, the oxazolylamine of formula (IX) is reacted with β-formyl-alkanoic ester of formula (XII) wherein R is ($C_1$-$C_4$)alkyl, phenyl or benzyl. This step is typically carried out using a variety of art recognized reaction conditions. For instance, it can be carried out in an organic solvent in the presence of a suitable base to form a compound of formula (XIII).

In Step 2, Scheme 2, the compound of formula (XIII) is then allowed to react with a compound of formula (VII) obtained in Step 2 of Scheme 1. Such substitution reactions are generally carried out similar to the procedures employed in Step 5, Scheme 1 as described above in order to obtain compound of formula (I).

Scheme 3 provides another approach for the preparation of the compounds of formula (I) wherein $R_1$ is hydrogen as illustrated in Scheme 1. In this approach the oxazolylamine of formula (IX) is first reacted with compound of formula (VII) which is further cyclized to form compounds of formula (I).

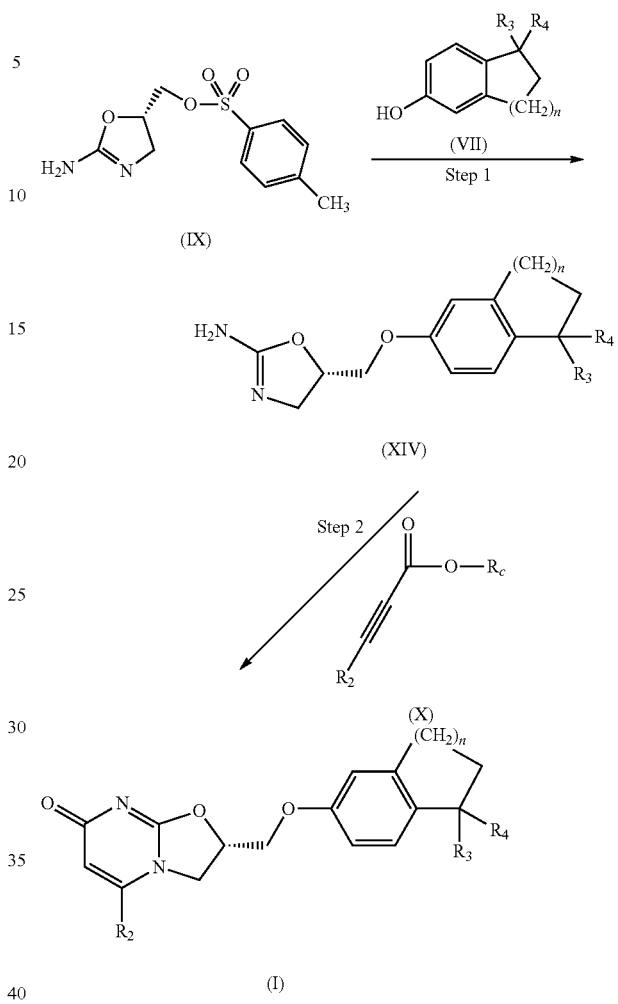

In Step 1, Scheme 3, the oxazolylamine of formula (IX) is first reacted with compound of formula (VII) using any of the art recognized procedures in a suitable organic solvent and temperature conditions to form compound of formula (XIV).

In Step 2, Scheme 3, the compound of formula (XIV) is then reacted with an α,β-unsaturated alkynoic ester of formula (X) to form the compound of formula (I). This reaction can again be carried out using similar procedures as described above in Step 4, Scheme 1.

Scheme 4 further illustrates another variation for the preparation of compounds of formula (I) of this invention. In this approach, a compound of formula (XIV) is reacted with β-formyl-alkanoic ester of formula (XII) wherein R is ($C_1$-$C_4$)alkyl, phenyl or benzyl. This step can be carried out using similar procedures as described above for Step 1, Scheme 2.

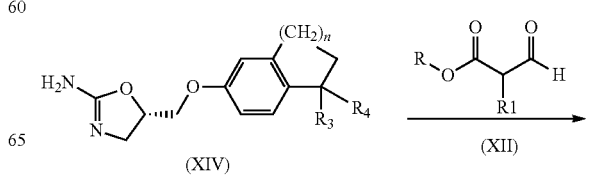

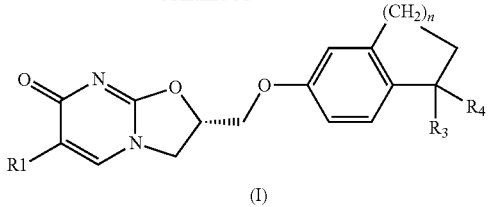

Scheme 5 further illustrates another approach for the preparation of compounds of formula (I) of this invention wherein $R_2$ is hydrogen.

In Step 1, Scheme 5, a compound of formula (VII) is reacted with an oxirane of formula (XV) in an organic solvent to form a compound of formula (XVI). This reaction can be carried out using any of the procedures known in the art. For example such reactions are generally carried out in a suitable organic solvent in the presence of a suitable base at ambient to super-ambient temperature conditions. Solvents that can be used in this step can be any of the solvents routinely used for such reactions. For instance, suitable solvents are ketones, such as acetone, methyl ethyl ketone (MEK) and the like. Suitable base for this reaction include but not limited to lithium carbonate, sodium carbonate, potassium carbonate, and the like. Generally, potassium carbonate is employed. It has been also observed that the temperature at which the reaction is carried out may control the stereoselectivity of this reaction. For example, a temperature of the reaction below 50° C. favors higher stereoselectivity. More specifically, a temperature range of about 40° C. to about 50° C. can be employed depending upon the solvent used and, the substituents on compound of formula (VII).

In step 2, Scheme 5, the resulting oxirane compound of formula (XVI) is reacted with a cyanamide compound to form oxazolyl amine of formula (XVII). This reaction can be carried out under similar reaction conditions as described above in Step 3, Scheme 1.

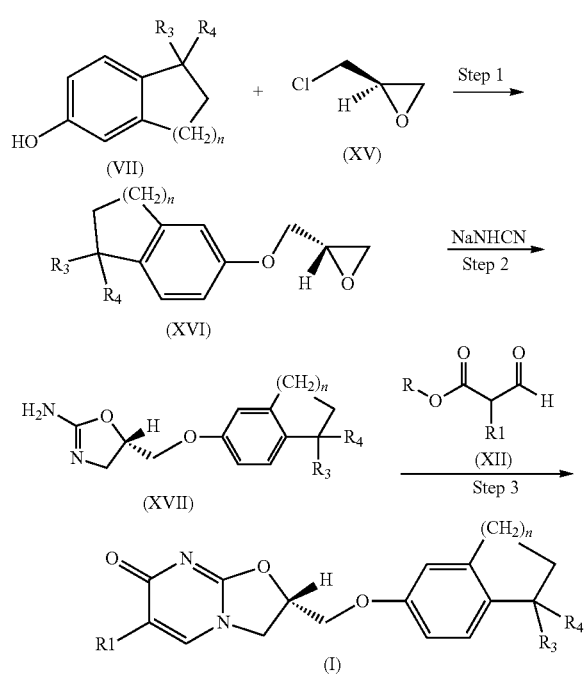

In Step 3, Scheme 5, the compound of formula (XVII) is reacted with β-formyl-alkanoic ester of formula (XII) wherein R is $(C_1-C_4)$alkyl, phenyl or benzyl to form compound of formula (I). This step can be carried out using similar procedures as described above in Step 1, Scheme 2.

Scheme 6 provides an alternative approach for the preparation of compounds of formula (I) wherein $R_1$ is hydrogen employing compound of formula (XVII) and α,β-unsaturated alkynoic ester of formula (X).

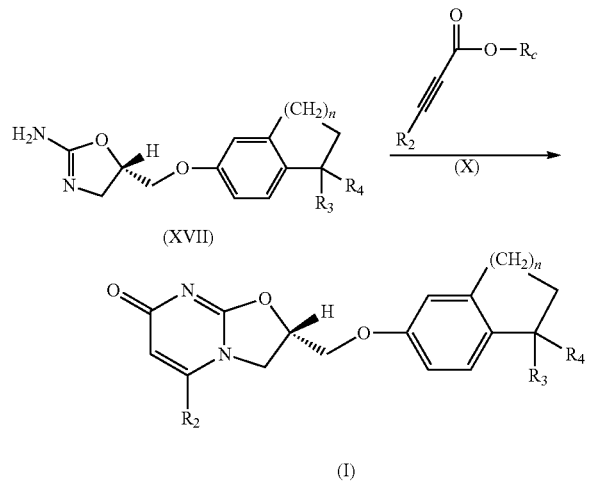

Several of the intermediate compounds described in Schemes 1-6 are either readily available and/or may be prepared using any of the procedures known in the art. For instance, Scheme 7 illustrates preparation of compound of formula (XII), which involves reaction of a carboxylic ester of formula (XVIII) with formyl ester. Such addition reactions can be carried out using any of the methods known in the art. For example, a carboxylic ester of formula (XVIII) is reacted first with alkyl lithium such as n-butyllithium in the presence of suitable base such as diisopropylamine and then reacted with an alkyl formate such as ethyl formate to form a compound of formula (XII). Such reactions can be carried out in any suitable organic solvents such as non-polar solvents including ether, hexanes, petroleum ether, and the like at sub-ambient, ambient or super-ambient reaction temperatures. Typically such reactions are carried out in inert atmosphere at sub-ambient temperature conditions.

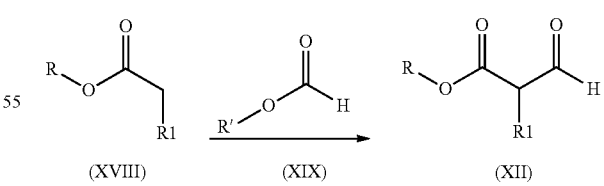

Scheme 8 further illustrates preparation of intermediate phenolic compounds similar to compound of formula (VII) which can be employed in one or more of the above schemes 1-6 in order to prepare compounds of formula (I) wherein $R_5$ is other than hydrogen. It should be understood that many variations of Scheme 8 can be employed to prepare other compounds of formula (XXII) wherein $R_5$ is as defined herein.

In Step 1, Scheme 8, a compound of formula (V) is brominated to form bromo-compound of formula (XX). However, any of the other known electrophilic substitution reactions can be carried out to make other substituted products within the definition of $R_5$. The bromination reaction as illustrated herein in Step 1, Scheme 8 can be carried out using any of the procedures known in the art. For instance, such bromination reactions can be carried out using N-bromosuccinimide in a suitable solvent such as water. The reaction can be carried out in solution or in suspension at any suitable reaction temperature and in the presence of a catalytic amounts of an acid such as sulfuric acid. Typically the reaction is carried out at superambient temperatures in the range of about 50° C. to 100° C.

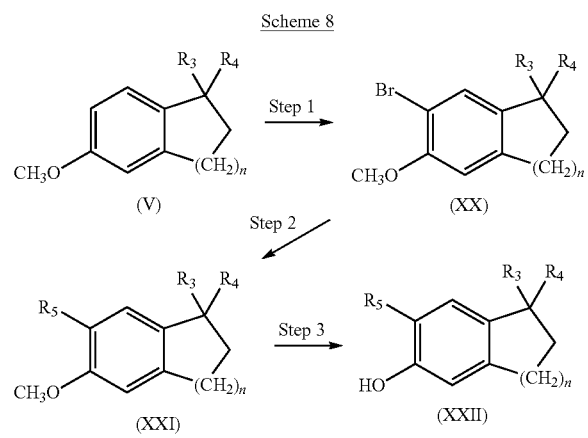

Scheme 8

In Step 2, Scheme 8, the bromo-compound of formula (XX) can further be converted to various other derivatives of formula (XXI) wherein a variety of desirable $R_5$ moieties can be introduced using methods known to one skilled in the art. For instance, bromo-compound of formula (XX) is lithiated with $(C_1-C_4)$alkyl lithium followed by reaction with the appropriate alkyl derivative such as an alkyl iodide or bromide to form compounds of formula (XXI) wherein $R_5$ is $(C_1-C_4)$alkyl.

In step 3, Scheme 8, the compound of formula (XXI) is subjected to demethylation reaction as discussed above in Step 2, Scheme 1 to obtain phenolic intermediate of formula (XXII) which can further be used in any of the Schemes 1-6 above in place of compound of formula (VII) to form a compound of formula (I) wherein $R_5$ is other than hydrogen as defined herein.

In another aspect of this embodiment, this invention also relates to a method of modulating one or more metabotropic glutamate receptor functions in a patient requiring such treatment. Such a method involves administering an effective amount of a compound of formula (I).

In this aspect of the embodiment of this invention the compounds of formula (I) of this invention are also useful in the preparation of a medicament for modulating one or more metabotropic glutamate receptor functions in a patient requiring such modulation. The medicaments can be prepared using any of the methods known in the art. For example, compounds of formula (I) can be mixed with one or more pharmaceutically excipients, diluents or carriers in order to form the medicament.

In a further embodiment, this invention also involves a method of treating a specific disease, a disorder or a condition using an effective amount of a compound of formula (I) of this invention. Specific diseases that can be treated using the compounds of formula (I) of this invention include, without any limitation, neurological or psychiatric disorders.

As used herein "psychiatric disorders" shall have the same meaning as "psychotic disorder" as defined in Diagnostic and Statistical Manual of Mental Disorders, $4^{th}$ Ed., ("DSM-IV") American Psychiatric Association, 1995, incorporated herein by reference. The essential feature of brief psychotic disorder is a disturbance that involves the sudden onset of at least one of the following positive psychotic symptoms: delusions, hallucinations, disorganized speech, (e.g., frequent derailment or incoherence), or grossly disorganized or catatonic behavior (Criterion A). An episode of the disturbance lasts at least one day but less than one month, and the individual eventually has a full return to the premorbid level of functioning (Criterion B). The disturbance is not better accounted for by a mood disorder with psychotic features, by schizoaffective disorder, or by schizophrenia and is not due to the direct physiological effects of a substance (e.g., hallucinogen) or a general medical condition (e.g., subdural hematoma) (Criterion C). It should further be noted that a skilled artisan recognizes that there are alternative nomenclatures, nosologies, and classification systems for neurological and psychiatric disorders described herein and that these systems evolve with medical scientific progress.

It is also recognized that one skilled in the art may affect the neurological and psychiatric disorders by treating a patient presently afflicted with the disorders or by prophylactically treating a patient afflicted with the disorders with an effective amount of the compound of formula (I) of this invention. Thus, the terms "treatment" and "treating" are intended to refer to all processes wherein there may be a slowing, interrupting, arresting, controlling, or stopping of the progression of the neurological and psychiatric disorders described herein, but does not necessarily indicate a total elimination of all disorder symptoms, and is intended to include prophylactic treatment of such neurological and psychiatric disorders.

In a further embodiment of this invention, specific diseases that can be treated using the compounds of formula (I) of this invention include without any limitation: anxiety, migraine, schizophrenia, epilepsy and pain.

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease involving the effects of metabotropic glutamate receptor functions. That is, the compounds of the present invention are modulators of metabotropic glutamate receptors (mGluR), particularly, mGluR2, and may be effectively administered to ameliorate any disease state which is mediated all or in part by mGluR2.

All of the various embodiments of the compounds used in the methods of this invention as disclosed herein can be used in the method of treating various disease states as described herein. As stated herein, the compounds used in the method of this invention are capable of modulating the effects of mGluR2 and thereby alleviating the effects and/or conditions caused due to the activity of mGluR2. In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal, intracerebroventricular (icv) or topical route.

Finally, in yet another embodiment of this invention, there is also provided a pharmaceutical composition comprising a pharmaceutically acceptable carrier and a compound of formula (I) of this invention, including pharmaceutically acceptable salts, solvates or derivatives thereof, with said compound having the general structure shown in formula I as described herein.

As described herein, the pharmaceutical compositions of this invention feature modulation of mGluR2 and thus are useful in treating any disease, condition or a disorder involving the effects of mGluR2 in a patient. Again, as described above, all of the preferred embodiments of the compounds of this invention as disclosed herein can be used in preparing the pharmaceutical compositions as described herein. Thus in accordance with this invention various compounds of formula (I) as described herein can be used in the preparation of pharmaceutical formulations for modulating the effects of mGluR2 and to treat all of the diseases as disclosed herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of formula (I) of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal, intracerebroventricular (icy) or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

Reactions generally are run under a nitrogen atmosphere. Solvents are dried over sodium or magnesium sulfate and are evaporated under vacuum on a rotary evaporator. TLC analyses are performed with EM Science silica gel 60 F254 plates with visualization by UV irradiation wherever possible. Flash chromatography is performed using Isco prepacked silica gel cartridges. The $^1$H NMR spectra are run at 300 MHz on a Gemin±300 or Varian VXR 300 spectrometer and are determined in a deuterated solvent, such as DMSO-$d_6$ or CDCl$_3$ unless otherwise noted. Chemical shifts values are indicated in parts per million (ppm) with reference to tetramethylsilane (TMS) as the internal standard. The LC/MS are run on a Micromass Platform LCZ.

As used in the examples and preparations that follow, the terms used therein shall have the meanings indicated: "kg" refers to kilograms, "g" refers to grams, "mg" refers to milligrams, "µg" refers to micrograms, "pg" refers to picograms, "lb" refers to pounds, "oz" refers to ounces, "mol" refers to moles, "mmol" refers to millimoles, "µmole" refers to micromoles, "nmole" refers to nanomoles, "L" refers to liters, "mL" or "ml" refers to milliliters, "µL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "THF" refers to tetrahydrofuran, "DMF" refers to dimethylformamide, "NMP" refers to 1-methyl-2-pyrrolidinone, "EtOH" refers to ethyl alcohol, "MeOH" refers to methyl alcohol, "EtOAc" refers to ethyl acetate; "brine" refers to a saturated aqueous sodium chloride solution, "M" refers to molar, "mM" refers to millimolar, "µM" refers to micromolar, "nM" refers to nanomolar, "N" refers to normal, "TLC" refers to thin layer chromatography, "HPLC" refers to high performance liquid chromatography, "i.p." refers to intraperitoneally, "i.v." refers to intravenously, anhyd=anhydrous; aq=aqueous; min=minute;

mins=minutes; h or hr=hour; d=day; psi=pounds per square inch; atm=atmosphere; sat.=saturated; s=singlet, d=doublet; t=triplet; q=quartet; m=multiplet; dd=doublet of doublets; br=broad; LC=liquid chromatograph; MS=mass spectrograph; ESI=electrospray ionization; CI=chemical ionization; RT=retention time; M=molecular ion. Optical rotations $[\alpha]_D^{25}$ were measured using a Perkin Elmer polarimeter model 341 with a sodium lamp, D line (589 nm), path length 100 mm at 25° C. temperature at a concentration (g/100 ml) and solvent as specified in the respective examples below.

Example 1

(S)-2-(1,1-Dimethyl-indan-5-yloxymethyl)-2,3-dihydro-oxazolo[3,2-a]pyrimidin-7-one

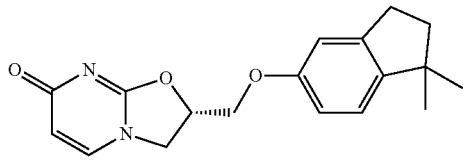 [SMILES: CC1(C)CCc2cc(OC[C@@H]3Cn4ccc(=O)nc4O3)ccc21]

Step 1: 1,1-Dimethyl-indan-5-ol

The title compound was prepared in two steps following the procedures described in U.S. Pat. Appl. Publ., 2006100460, employing 5-methoxy-indan-1-one as the starting material.

$C_{11}H_{14}O$ (162.10), LCMS (ESI): 163.11 (M$^+$+H).

$^1$H NMR (CDCl$_3$, 300 MHz), δ 6.98 (d, 1H), 6.66 (s, 1H), 6.64 (d, 1H), 4.51 (s, 1H), 2.83 (t, 2H), 1.92 (t, 2H), 1.23 (s, 6H).

Step 2: (S)-2-(1,1-Dimethyl-indan-5-yloxymethyl)-2,3-dihydro-oxazolo[3,2-a]pyrimidin-7-one To a solution of (S)-2-toluene-4-sulfonic acid methyl-2,3-dihydro-oxazolo[3,2-a]pyrimidin-7-one (0.8 g, 2.48 mmol) (prepared in accordance with the procedures described in WO 2008/112483) in acetonitrile (80 ml) was added 1,1-dimethyl-indan-5-ol (0.4 g, 2.48 mmol), followed by addition of cesium carbonate (0.82 g, 2.48 mmol). The reaction mixture was stirred at reflux for 1 hour. It was then concentrated and the residue was dissolved in ethyl acetate/water. The whole was extracted with ethyl acetate. The organic phase was washed successively with 3 percent hydrochloric acid, saturated NaHCO$_3$, brine, and dried (Na$_2$SO$_4$). Silica gel chromatography (silica, 7N NH$_3$ in methanol/methylene chloride) provided 0.4 g (47%) of the title compound. $[\alpha]_D^{25}$=−55.0 (c=1.11, CHCl$_3$).

$C_{18}H_{20}N_2O_3$ (312.14), LCMS (ES$^+$): 313.14 (M$^+$+H).

$^1$H NMR (CDCl$_3$, 300 MHz), δ 7.24 (d, 1H), 7.03 (d, 1H), 6.72 (s, 1H), 6.69 (d, 1H), 6.08 (d, 1H), 5.27 (m, 1H), 4.20~4.41 (m, 4H), 2.84 (t, 2H), 1.92 (t, 2H), 1.23 (s, 6H).

Example 2

(S)-2-(5,5-Dimethyl-5,6,7,8-tetrahydro-naphthalen-2-yloxymethyl)-2,3-dihydro-oxazolo[3,2-a]pyrimidin-7-one

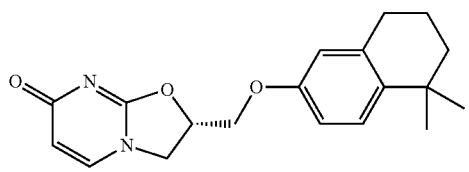 [SMILES: CC1(C)CCCc2cc(OC[C@@H]3Cn4ccc(=O)nc4O3)ccc21]

Step 1: 5,5-Dimethyl-5,6,7,8-tetrahydro-naphthalen-2-ol

The title compound was prepared in two steps following the procedures described in U.S. Pat. Appl. Publ., 2006100460, employing 6-methoxy-3,4-dihydro-2H-naphthalen-1-one as the starting material.

$C_{12}H_{16}O$ (176.12), LCMS (ES$^+$): 177.14 (M$^+$+H).

$^1$H NMR (CDCl$_3$, 300 MHz), δ 7.19 (d, 1H), 6.64 (dd, 1H), 6.51 (d, 1H), 4.46 (s, 1H), 2.70 (t, 2H), 1.79 (m, 2H), 1.63 (m, 2H), 1.26 (s, 6H).

Step 2: (S)-2-(5,5-Dimethyl-5,6,7,8-tetrahydro-naphthalen-2-yloxymethyl)-2,3-dihydro-oxazolo[3,2-a]pyrimidin-7-one The title compound was prepared from 5,5-dimethyl-5,6,7,8-tetrahydro-naphthalen-2-ol employing the procedure described in Example 1. $[\alpha]_D^{25}$=−58.0 (c=0.87, CHCl$_3$).

$C_{19}H_{22}N_2O_3$ (326.16), LCMS (ES$^+$): 327.16 (M$^+$+H).

$^1$H NMR (CDCl$_3$, 300 MHz), δ 7.24 (m, 2H), 6.68 (dd, 1H), 6.55 (d, 1H), 6.06 (d, 1H), 5.26 (m, 1H), 4.18~4.41 (m, 4H), 2.71 (t, 2H), 1.78 (m, 2H), 1.63 (m, 2H), 1.25 (s, 6H).

Example 3

(S)-2-(5,5-Dimethyl-6,7,8,9-tetrahydro-5H-benzocyclohepten-2-yloxymethyl)-2,3-dihydro-oxazolo[3,2-a]pyrimidin-7-one

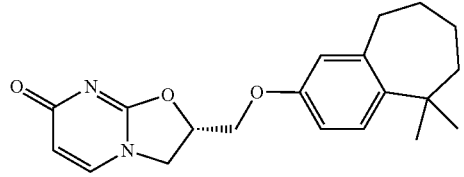 [SMILES: CC1(C)CCCCc2cc(OC[C@@H]3Cn4ccc(=O)nc4O3)ccc21]

Step 1: 5,5-Dimethyl-6,7,8,9-tetrahydro-5H-benzocyclohepten-2-ol

The title compound was prepared in two steps following the procedures described in U.S. Pat. Appl. Publ., 2006100460, employing 2-methoxy-6,7,8,9-tetrahydro-benzocyclohepten-5-one as the starting material.

$C_{13}H_{18}O$ (190.14), LCMS (ES$^+$): 191.15 (M$^+$+H).

$^1$H NMR (CDCl$_3$, 300 MHz), δ 7.22 (d, 1H), 6.59 (dd, 1H), 6.57 (s, 1H), 4.49 (s, 1H), 2.87 (m, 2H), 1.84 (m, 2H), 1.64 (m, 4H), 1.35 (s, 6H).

Step 2: (S)-2-(5,5-Dimethyl-6,7,8,9-tetrahydro-5H-benzocyclohepten-2-yloxymethyl)-2,3-dihydro-oxazolo[3,2-a]pyrimidin-7-one The title compound was prepared from 5,5-dimethyl-6,7,8,9-tetrahydro-5H-benzocyclohepten-2-ol employing the procedure described in Example 1. $[\alpha]_D^{25}=-64.4$ (c=0.68, CHCl$_3$).

$C_{20}H_{24}N_2O_3$ (340.17), LCMS (ESI): 341.15 (M$^+$+H).

$^1$H NMR (CDCl$_3$, 300 MHz), δ 7.25 (m, 2H), 6.63 (dd, 1H), 6.61 (s, 1H), 6.10 (d, 1H), 5.26 (m, 1H), 4.19~4.40 (m, 4H), 2.88 (m, 2H), 1.84 (m, 2H), 1.64 (m, 4H), 1.34 (s, 6H).

Example 4

(S)-2-(5,5,8,8-Tetramethyl-5,6,7,8-tetrahydro-naphthalen-2-yloxymethyl)-2,3-dihydro-oxazolo[3,2-a]pyrimidin-7-one

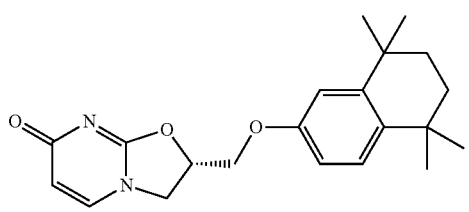 [SMILES: CC1(C)CCC(C)(C)c2cc(OC[C@@H]3Cn4ccc(=O)nc4O3)ccc21]

Step 1: 5,5,8,8-Tetramethyl-5,6,7,8-tetrahydro-naphthalen-2-ol

6-Methoxy-1,1,4,4-tetramethyl-1,2,3,4-tetrahydro-naphthalene was prepared employing the procedures described in U.S. Pat. Appl. Publ. 2005/0148590 A1, employing 2,5-dimethyl-hexane-2,5-diol and anisole as the starting materials. 6-Methoxy-1,1,4,4-tetramethyl-1,2,3,4-tetrahydro-naphthalene was subsequently treated with BBr$_3$ in CH$_2$Cl$_2$ to provide the title compound.

$C_{14}H_{20}O$ (204.15), LCMS (ES$^+$): 205.16 (M$^+$+H).

$^1$H NMR (CDCl$_3$, 300 MHz), δ 7.17 (d, 1H), 6.76 (d, 1H), 6.62 (dd, 1H), 4.45 (s, 1H), 1.66 (s, 4H), 1.26 (s, 6H), 1.25 (s, 6H).

Step 2: (S)-2-(5,5,8,8-Tetramethyl-5,6,7,8-tetrahydro-naphthalen-2-yloxymethyl)-2,3-dihydro-oxazolo[3,2-a]pyrimidin-7-one The title compound was prepared from 5,5,8,8-tetramethyl-5,6,7,8-tetrahydro-naphthalen-2-ol employing the procedure described in Example 1. $[\alpha]_D^{25}=-58.2$, (c=0.97, CHCl$_3$)

$C_{21}H_{26}N_2O_3$ (354.19), LCMS (ES$^+$): 355.19 (M$^+$+H).

$^1$H NMR (CDCl$_3$, 300 MHz), δ 7.24 (m, 2H), 6.80 (d, 1H), 6.68 (dd, 1H), 6.09 (d, 1H), 5.27 (m, 1H), 4.21~4.41 (m, 4H), 1.67 (s, 4H), 1.26 (s, 6H). 1.25 (s, 6H).

Example 5

(S)-2-(6-Bromo-1,1-dimethyl-indan-5-yloxymethyl)-2,3-dihydro-oxazolo[3,2-a]pyrimidin-7-one

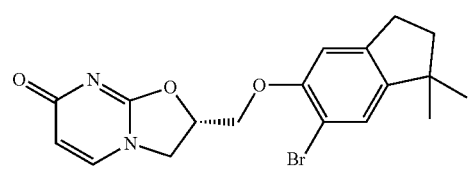 [SMILES: CC1(C)CCc2cc(OC[C@@H]3Cn4ccc(=O)nc4O3)c(Br)cc21]

Step 1: 6-Bromo-5-methoxy-1,1-dimethyl-indan

To a suspension of 5-methoxy-1,1-dimethyl-indan (2.16 g, 12.25 mmol) (prepared following the procedures described in U.S. Pat. Appl. Publ., 2006100460) in water (120 ml), NBS (2.2 g, 12.3 mmol) was added. The reaction mixture was heated to 60° C. while stirring. Concentrated H$_2$SO$_4$ (1.3 ml, 40% aq. solution) was then added and stirring was continued for 5 hours. The reaction mixture was cooled to rt. The mixture was extracted with diethyl ether three times. The combined organic extract was washed with brine and dried (Na$_2$SO$_4$). Silica gel chromatography (ethyl acetate/heptane) provided 2.78 g (89%) of the title compound.

$C_{12}H_{15}BrO$ (254.03), LCMS (EI$^+$): 254.04 (M$^+$).

$^1$H NMR (CDCl$_3$, 300 MHz), δ 7.26 (s, 1H), 6.76 (s, 1H), 3.86 (s, 3H), 2.83 (t, 2H), 1.93 (t, 2H), 1.22 (s, 6H).

Step 2: 6-Bromo-1,1-dimethyl-indan-5-ol

To 6-bromo-5-methoxy-1,1-dimethyl-indan (0.6 g, 2.35 mmol) in CH$_2$Cl$_2$ (30 mL) was added BBr$_3$ (1M in CH$_2$Cl$_2$, 4.70 mmol) dropwise at −78° C. Following addition the mixture was allowed to warm to room temperature and subsequently stirred at room temperature for 2 h. The reaction mixture was then quenched with MeOH (5 mL). Aqueous sodium hydrogen carbonate (10 mL) was added. The reaction mixture was stirred at room temperature for 1 hour. The reaction mixture was extracted with CH$_2$Cl$_2$. The organic phase was washed with brine, dried (Na$_2$SO$_4$) and concentrated. Silica gel chromatography (EtOAc/heptane) provided 0.51 g (90%) of 6-bromo-1,1-dimethyl-indan-5-ol.

$C_{11}H_{13}BrO$ (240.01), LCMS (EI$^+$): 240.01 (M$^+$).

$^1$H NMR (CDCl$_3$, 300 MHz), δ 7.16 (s, 1H), 6.84 (s, 1H), 5.33 (s, 1H), 2.81 (t, 2H), 1.92 (t, 2H), 1.22 (s, 6H).

Step 3: (S)-2-(6-Bromo-1,1-dimethyl-indan-5-yloxymethyl)-2,3-dihydro-oxazolo[3,2-a]pyrimidin-7-one The title compound was prepared from 6-bromo-1,1-dimethyl-indan-5-ol employing the procedure described in Example 1. $[\alpha]_D^{25}=-24.2$ (c=0.98, CHCl$_3$).

$C_{18}H_{19}BrN_2O_3$ (390.06), LCMS (ES$^+$): 391.03 (M$^+$+H).

$^1$H NMR (CDCl$_3$, 300 MHz), δ 7.26 (d, 1H), 7.22 (s, 1H), 6.76 (s, 1H), 6.06 (d, 1H), 5.29 (m, 1H), 4.34~4.50 (m, 3H), 4.22 (dd, 1H), 2.82 (t, 2H), 1.93 (t, 2H), 1.22 (s, 6H).

Example 6

(S)-2-(1,1,6-Trimethyl-indan-5-yloxymethyl)-2,3-dihydro-oxazolo[3,2-a]pyrimidin-7-one

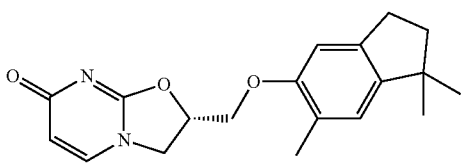 [SMILES: Cc1cc2c(cc1OC[C@@H]1Cn3ccc(=O)nc3O1)CCC2(C)C]

Step 1: 5-Methoxy-1,1,6-trimethyl-indan

The title compound was prepared in accordance with the procedure described in Synthetic Communications, 31 (15), 2323-2327, employing 6-bromo-5-methoxy-1,1-dimethyl-indan as the starting material.

$C_{13}H_{18}O$ (190.13), LCMS (ESI): 191.15 (M$^+$+H).
$^1$H NMR (CDCl$_3$, 300 MHz), δ 6.89 (s, 1H), 6.69 (s, 1H), 3.81 (s, 3H), 2.85 (t, 2H), 2.20 (s, 3H), 1.91 (t, 2H), 1.23 (s, 6H).

Step 2: 1,1,6-Trimethyl-indan-5-ol

The title compound was prepared from 5-methoxy-1,1,6-trimethyl-indan employing the procedure described in Step 2 of Example 5.

$C_{12}H_{16}O$ (176.12), LCMS (ES$^+$): 177.14 (M$^+$+H).
$^1$H NMR (CDCl$_3$, 300 MHz), δ 6.87 (s, 1H), 6.62 (s, 1H), 4.48 (s, 1H), 2.80 (t, 2H), 2.23 (s, 3H), 1.90 (t, 2H), 1.22 (s, 6H).

Step 3: (S)-2-(1,1,6-Trimethyl-indan-5-yloxymethyl)-2,3-dihydro-oxazolo[3,2-a]pyrimidin-7-one The title compound was prepared from 1,1,6-trimethyl-indan-5-ol employing the procedure described in Example 1. [α]$_D^{25}$=−30.5 (c=0.61, CHCl$_3$).

$C_{19}H_{22}N_2O_3$ (326.16), LCMS (ES$^+$): 327.15 (M$^+$+H).
$^1$H NMR (CDCl$_3$, 300 MHz), δ 7.24 (d, 1H), 6.88 (s, 1H), 6.64 (s, 1H), 6.08 (d, 1H), 5.29 (m, 1H), 4.15~4.43 (m, 4H), 2.83 (t, 2H), 2.03 (s, 3H), 1.90 (t, 2H), 1.21 (s, 6H).

Example 7

(S)-2-(1,1-Dimethyl-indan-5-yloxymethyl)-6-ethyl-2,3-dihydro-oxazolo[3,2-a]pyrimidin-7-one

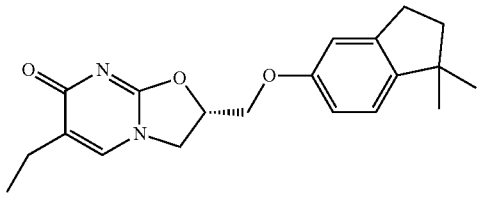 [SMILES: CCc1cn2c(nc1=O)O[C@H](COc1ccc3c(c1)CCC3(C)C)C2]

Step 1: 2-Formyl-butyric acid ethyl ester

A solution of diisopropylamine (10.1 g, 100 mmol) in THF (100 mL) was treated with n-butyllithium (1.6 M in hexane, 63 mL, 100 mmol) at room temperature under N$_2$. The resulting pale yellow solution was cooled to −78° C. A solution of butyric acid ethyl ester (10.4 g, 89.2 mmol) in THF (28 mL) was added. Stirring was continued for a half hour at −78° C., after which ethyl formate (22.0 g, 300 mmol) was added. The reaction mixture was allowed to warm to room temperature and stirred for three hours under N$_2$. The reaction mixture was quenched with acetic acid (~17 ml), diluted with diethyl ether, washed with water, brine, dried (Na$_2$SO$_4$). Silica gel chromatography (methyl acetate/hexane) provided 12.5 g of the title compound as a mixture of isomers.

$C_7H_{12}O_3$ (144.08), LCMS (ES$^+$): 145.08 (M$^+$+H).

Step 2: (S)-2-(1,1-Dimethyl-indan-5-yloxymethyl)-oxirane

To a mixture of (R)-epichlorohydrin (0.93 g, 10 mmol) and 1,1-dimethyl-indan-5-ol (0.81 g, 5.0 mmol) in acetone (30 ml) was added potassium carbonate (0.69 g, 5 mmol). The mixture was stirred at 45° C. for 96 hours. The reaction mixture was then concentrated. The residue was partitioned between ethyl acetate and water and extracted twice with ethyl acetate. The organic phases were combined and washed with water, brine, dried over sodium sulfate and concentrated under vacuum. The resulting residue was purified by flash chromatography (silica, methylene chloride/heptane) to give 9.18 g (67%) of (S)-2-(1,1-dimethyl-indan-5-yloxymethyl)-oxirane.

$C_{14}H_{18}O_2$ (218.13), LCMS (ES$^+$): 260.14 (M$^+$+H+CH$_3$CN).
$^1$H NMR (CDCl$_3$, 300 MHz), δ 7.02 (d, 1H), 6.76 (s, 1H), 6.74 (d, 1H), 4.16 (dd, 1H), 3.96 (dd, 1H), 3.34 (m, 1H), 2.81~2.92 (m, 3H), 2.74 (dd, 1H), 1.92 (t, 2H), 1.23 (s, 6H).

Step 3: 5-(1,1-Dimethyl-indan-5-yloxymethyl)-4,5-dihydro-oxazol-2-ylamine

To a vigorously stirred solution of sodium hydrogen cyanamide (0.21 g, 3.21 mmol) in methanol (10 mL) was added slowly (S)-2-(1,1-dimethyl-indan-5-yloxymethyl)-oxirane (0.57 g, 3.21 mmol). The reaction mixture was stirred at room temperature overnight after which the reaction mixture was concentrated. Anhydrous diethyl ether (50 mL) was added. The resulting white precipitate was filtered through Celite and the filtrate concentrated. The residue was purified by flash chromatography (silica, 7N NH$_3$ in methanol/methylene chloride) to give 0.41 g (49%) of 5-(1,1-dimethyl-indan-5-yloxymethyl)-4,5-dihydro-oxazol-2-ylamine.

$C_{15}H_{20}N_2O_2$ (260.15), LCMS (ES$^+$): 261.14 (M$^+$+H).
$^1$H NMR (CDCl$_3$, 300 MHz), δ 7.03 (d, 1H), 6.76 (s, 1H), 6.74 (d, 1H), 4.91 (m, 1H), 3.86~4.11 (m, 3H), 3.60 (dd, 1H), 2.85 (t, 2H), 1.92 (t, 2H), 1.23 (s, 6H).

Step 4: (S)-2-(1,1-Dimethyl-indan-5-yloxymethyl)-6-ethyl-2,3-dihydro-oxazolo[3,2-a]pyrimidin-7-one To a solution of 5-(1,1-dimethyl-indan-5-yloxymethyl)-4,5-dihydro-oxazol-2-ylamine (0.41 g, 1.57 mmol) in ethanol (16 mL) was added 2-formyl-butyric acid ethyl ester (0.34 g, 2.23 mmol). The reaction mixture was heated at reflux for 20 hours. It was then concentrated and loaded on a silica gel column. Chromatography with (1-5%) 2-propanol/methylene chloride gave 0.092 g of the title product. [α]$_D^{25}$=−24.1 (c=0.76, CHCl$_3$).

$C_{20}H_{24}N_2O_3$ (340.18), LCMS (ES$^+$): 341.15 (M$^+$+H).

$^1$H NMR (CDCl$_3$, 300 MHz), δ 7.04 (s, 1H), 7.02 (d, 1H), 6.72 (s, 1H), 6.69 (d, 1H), 5.24 (m, 1H), 4.21~4.41 (m, 4H), 2.84 (t, 2H), 2.43 (q, 2H), 1.92 (t, 2H), 1.22 (s, 6H) 1.15 (t, 3H).

Example 8

(S)-2-(5,5-Dimethyl-5,6,7,8-tetrahydro-naphthalen-2-yloxymethyl)-6-ethyl-2,3-dihydro-oxazolo[3,2-a]pyrimidin-7-one

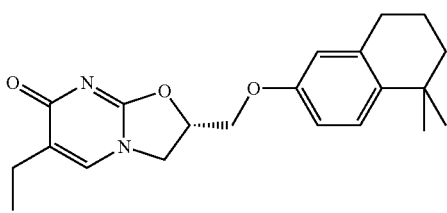 [SMILES: CCc1cn2c(nc1=O)O[C@H](COc1ccc3c(c1)CCCC3(C)C)C2]

Step 1: (S)-2-(5,5-Dimethyl-5,6,7,8-tetrahydro-naphthalen-2-yloxymethyl)-oxirane To a mixture of (R)-epichlorohydrin (2.2 g, 23.8 mmol) and 5,5-dimethyl-5,6,7,8-tetrahydro-naphthalen-2-ol (2.1 g, 11.9 mmol) in acetone (30 ml) was added potassium carbonate (1.65 g, 11.9 mmol). The mixture was stirred at 45° C. for 7 days. The reaction mixture was then concentrated. The residue was partitioned between ethyl acetate and water and extracted twice with ethyl acetate. The organic extracts were combined and washed with water, brine, dried over sodium sulfate and concentrated under vacuum. The resulting residue was purified by flash chromatography (silica, methylene chloride/heptane) to give 1.84 g (67%) of (S)-2-(5,5-dimethyl-5,6,7,8-tetrahydro-naphthalen-2-yloxymethyl)-oxirane.

$C_{15}H_{20}O_2$ (232.15), LCMS (ES$^+$): 274.15 (M$^+$+H+CH$_3$CN).

$^1$H NMR (CDCl$_3$, 300 MHz), δ 7.23 (d, 1H), 6.74 (dd, 1H), 6.59 (d, 1H), 4.15 (dd, 1H), 3.95 (dd, 1H), 3.33 (m, 1H), 2.89 (t, 1H), 2.73 (m, 3H), 1.79 (m, 2H), 1.64 (m, 2H), 1.26 (s, 6H).

Step 2: 5-(5,5-Dimethyl-5,6,7,8-tetrahydro-naphthalen-2-yloxymethyl)-4,5-dihydro-oxazol-2-ylamine To a vigorously stirred solution of sodium hydrogen cyanamide (0.52 g, 7.9 mmol) in methanol (20 mL) was added slowly (S)-2-(5,5-dimethyl-5,6,7,8-tetrahydro-naphthalen-2-yloxymethyl)-oxirane (1.8 g, 7.9 mmol). The reaction mixture was stirred at room temperature overnight after which it was concentrated. Anhydrous diethyl ether (100 mL) was added. The resulting white precipitate was filtered and the filtrate concentrated. The residue was purified by flash chromatography (silica, 7N NH$_3$ in methanol/methylene chloride) to give 1.0 g (46%) of 5-(5,5-dimethyl-5,6,7,8-tetrahydro-naphthalen-2-yloxymethyl)-4,5-dihydro-oxazol-2-ylamine.

$C_{16}H_{22}N_2O_2$ (274.17), LCMS (ES$^+$): 275.14 (M$^+$+H).

$^1$H NMR (CDCl$_3$, 300 MHz), δ 7.24 (d, 1H), 6.73 (dd, 1H), 6.60 (d, 1H), 4.90 (m, 1H), 3.85~4.09 (m, 3H), 3.59 (dd, 1H), 2.73 (t, 2H), 1.79 (m, 2H), 1.65 (m, 2H), 1.25 (s, 6H).

Step 3: (S)-2-(5,5-Dimethyl-5,6,7,8-tetrahydro-naphthalen-2-yloxymethyl)-6-ethyl-2,3-dihydro-oxazolo[3,2-a]pyrimidin-7-one To a solution of 5-(5,5-dimethyl-5,6,7,8-tetrahydro-naphthalen-2-yloxymethyl)-4,5-dihydro-oxazol-2-ylamine (0.5 g, 1.82 mmol) in ethanol (16 mL) was added 2-formyl-butyric acid ethyl ester (0.39 g, 2.7 mmol). The reaction mixture was stirred at room temperature for one hour, and then heated at reflux for 24 hours. It was then concentrated and loaded on a silica gel column. Chromatography with (1-5%) 2-propanol/methylene chloride gave 0.15 g the title product. $[α]_D^{25}$=−26.8 (c=0.74, CHCl$_3$).

$C_{21}H_{26}N_2O_3$ (354.19), LCMS (ES$^+$): 355.15 (M$^+$+H).

$^1$H NMR (CDCl$_3$, 300 MHz), δ 7.24 (d, 1H), 7.04 (s, 1H), 6.68 (dd, 1H), 6.55 (s, 1H), 5.23 (m, 1H), 4.36 (t, 1H), 4.29~4.40 (m, 3H), 2.72 (t, 2H), 2.44 (q, 2H), 1.78 (m, 2H), 1.64 (m, 2H), 1.25 (s, 6H), 1.15 (t, 3H).

Example 9

(S)-5-(1,1-Difluoro-propyl)-2-(1,1-dimethyl-indan-5-yloxymethyl)-2,3-dihydro-oxazolo[3,2-a]pyrimidin-7-one

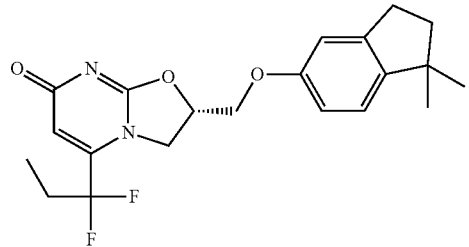 [SMILES: CCC(F)(F)c1cc(=O)nc2n1C[C@@H](COc1ccc3c(c1)CCC3(C)C)O2]

Step 1: (S)-5-(toluene-4-sulfonic acid methyl)-(4,5-dihydro-oxazol-2-yl)amine

To a vigorously stirred solution of sodium hydrogen cyanamide (2.81 g, 43.8 mmol) in methanol (44 mL) was added dropwise (2S)-glycidyl tosylate (10 g, 43.8 mmol) in methanol. The reaction mixture was stirred at room temperature overnight after which the reaction mixture was concentrated to remove methanol. Ethyl acetate was added (150 mL) along with 50 ml of water. The contents were transferred to a reparatory funnel, the organic layer was removed, dried over Na$_2$SO$_4$ and concentrated under vacuum to give 5.74 g (48%) of (S)-5-(toluene-4-sulfonic acid methyl)-(4,5-dihydro-oxazol-2-yl)amine.

$^1$H NMR (CDCl$_3$, 300 MHz), δ 7.83 (d, 2H), 7.39 (d, 2H), 4.80-4.70 (m, 1H), 4.15-4.10 (m, 1H), 3.83 (dd, 1H), 3.09-2.99 (m, 2H), 2.46 (s, 3H).

Step 2: 4-Oxo-hex-2-ynoic acid methyl ester

To a solution of 4-Hydroxy-hex-2-ynoic acid methyl ester (1.50 g, 10.55 mmol) in dichloromethane (30 mL) was added Des-martin periodinane (6.0 g, 14.14 mmol) and stirred at room temperature for 18 hours. Additional periodinane (4.5 g) was added to the reaction mixture and stirred at room temperature for 6 hours. Aqueous NaHCO3 was added to reaction mixture, and precipitate was filtered and washed with dichloromethane. Aqueous phase was extracted with dichloromethane, and combined organic phase was washed with water, brine, dried over Na₂SO₄, filtered and concentrated under vacuum to afford 1.48 g (100%) of title compound. C₇H₈O₃ (140.04)

¹H NMR ((CDCl₃), 300 MHz): δ 3.84 (s, 3H), 2.70-2.63 (q, 2H), 1.19-1.14 (t, 3H).

Step 3: 4,4-Difluoro-hex-2-ynoic acid methyl ester

To a solution of 4-Oxo-hex-2-ynoic acid methyl ester (1.48 g, 10.55 mmol) in dichloromethane (100 mL) was added diethylaminosulfur trifluoride (DAST) (5.1 g, 31.7 mmol) and stirred at room temperature for 18 hours. Reaction mixture was poured onto chopped ices and stirred for a few hours, then transferred to a separatory funnel. Aqueous phase was extracted with dichloromethane, and combined organic phase was washed with water, brine, dried over Na₂SO₄, filtered and concentrated under vacuum to afford 1.45 g (85%) of title compound. C₇H₈F₂O₂ (162.04)

¹H NMR ((CDCl₃), 300 MHz): δ 3.84 (s, 3H), 2.15-2.05 (m, 2H), 1.14-1.09 (t, 3H).

Step 4: Toluene-4-sulfonic acid (S)-5-(1,1-difluoro-propyl)-7-oxo-2,3-dihydro-7H-oxazolo[3,2-a]pyrimidin-2-ylmethyl ester To a solution of (S)-5-(toluene-4-sulfonic acid methyl)-(4,5-dihydro-oxazol-2-yl)amine (2.17 g, 8.02 mmol) in ethanol (10 mL) was added 4,4-difluoro-hex-2-ynoic acid methyl ester (1.30 g, 8.02 mmol). The reaction mixture was stirred at reflux for 2.5 hours. The mixture was cooled to room temperature, concentrated under vacuum, and purified by column chromatography on silica gel (0-10%) methanol in dichloromethane. This afforded 0.75 g (23%) of title compound. C₁₇H₁₈F₂N₂O₅S (400.09), LCMS (ES⁺): 401.10 (M⁺+H).

¹H NMR ((CDCl₃), 300 MHz): δ 7.77-7.75 (d, 2H), 7.39-7.36 (d, 2H), 6.17 (s, 1H), 5.16-5.09 (m, 1H), 4.50-4.44 (t, 1H), 4.34-4.29 (m, 3H), 2.47 (s, 3H), 2.29-2.12 (m, 2H), 1.17-1.12 (t, 3H).

Step 5: (S)-5-(1,1-Difluoro-propyl)-2-(1,1-dimethyl-indan-5-yloxymethyl)-2,3-dihydro-oxazolo[3,2-a]pyrimidin-7-one To a solution of toluene-4-sulfonic acid (S)-5-(1,1-difluoro-propyl)-7-oxo-2,3-dihydro-7H-oxazolo[3,2-a]pyrimidin-2-ylmethyl ester (75 mg, 0.188 mmol) in acetonitrile (6 mL) was added 1,1-Dimethyl-indan-5-ol (46 mg, 0.281 mmol) followed by cesium carbonate (107 mg, 0.325 mmol). The reaction mixture was stirred at reflux until complete. The reaction mixture cooled to room temperature, diluted with ethyl acetate, washed with water, dried over Na₂SO₄, filtered and concentrated under vacuum. Material purified by column chromatography on silica gel (0-10%) methanol in dichloromethane. This afforded 29.6 mg (41%) of the title compound. C₂₁H₂₄F₂N₂O₃ (390.17), LCMS (ES⁻): 391.17 (M⁺+H).

¹H NMR ((CDCl₃), 300 MHz): δ 6.97-6.95 (d, 1H), 6.63-6.59 (d, 2H), 6.16 (s, 1H), 5.18-5.13 (m, 1H), 4.43-4.38 (t, 1H), 4.28-4.23 (dd, 1H), 4.16-4.12 (dd, 1H), 2.80-2.75 (t, 2H), 2.27-2.09 (m, 2H), 1.88-1.83 (t, 2H), 1.16 (s, 6H), 1.13-1.07 (m, 3H).

Example 10

(S)-5-(1,1-Difluoro-propyl)-2-(5,5-dimethyl-5,6,7,8-tetrahydro-naphthalen-2-yloxymethyl)-2,3-dihydro-oxazolo[3,2-a]pyrimidin-7-one

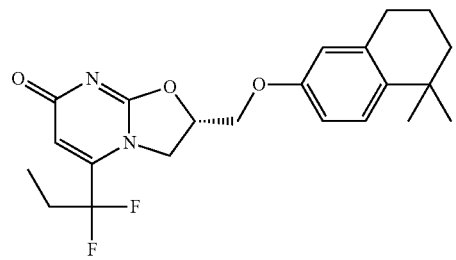 [SMILES: CCC(F)(F)c1cc(=O)nc2n1C[C@@H](COc1ccc3c(c1)CCCC3(C)C)O2]

The title compound was prepared from toluene-4-sulfonic acid (S)-5-(1,1-difluoro-propyl)-7-oxo-2,3-dihydro-7H-oxazolo[3,2-a]pyrimidin-2-ylmethyl ester (0.188 mmol) and 5,5-dimethyl-5,6,7,8-tetrahydro-naphthalen-2-ol (0.281, mmol,) according to the procedure described in Example 9. This afforded 24.0 mg (32%) of title compound.

C₂₂H₂₆F₂N₂O₃ (404.19), LCMS (ES): 405.17 (M⁺+H).

¹H NMR ((CDCl₃), 300 MHz): δ 7.25-7.22 (d, 1H), 6.68-6.65 (d, 1H), 6.54 (s, 1H), 6.23 (s, 1H), 5.25-5.18 (m, 1H), 4.49-4.40 (m, 2H), 4.34-4.30 (dd, 1H), 4.22-4.19 (dd, 1H), 2.74-2.70 (t, 2H), 2.32-2.16 (m, 1H), 1.81-1.77 (m, 2H), 1.65-1.62 (m, 2H), 1.25 (s, 6H), 1.17-1.14 (t, 3H).

Example 11

(S)-2-(6-Fluoro-1,1-dimethyl-indan-5-yloxymethyl)-2,3-dihydro-oxazolo[3,2-a]pyrimidin-7-one

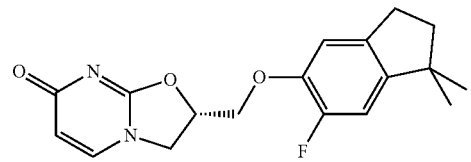 [SMILES: CC1(C)CCc2cc(OC[C@@H]3Cn4ccc(=O)nc4O3)c(F)cc21]

Step 1: 6-Fluoro-5-methoxy-1,1-dimethyl-indan

To a solution of 6-bromo-5-methoxy-1,1-dimethyl-indan (2.77 g, 10.8 mmol) (see Example 5) in THF (40 mL) at −78° C. was slowly added n-butyllithium (5.56 ml, 2.5M). The resulting solution was stirred at −78° C. for 0.5 h and a solution of N-fluorobenzenesulfonimide (4.11 g, 13.0 mmol) in THF (40 mL) was added. After an additional 2 h at −78° C., the reaction was warmed to room temperature, poured into water (50 mL), and extracted with ethyl acetate (2×80 mL). The combined organic layers were washed with water (100 mL), dried over sodium sulfate, filtered, and concentrated. Silica gel chromatography (2% ethyl acetate/heptanes) afforded 1.40 g of the title compound as yellow oil.

C₁₂H₁₅FO, (194.11), MS (EI⁺): 194.13 (M⁺)

Step 2: 6-Fluoro-1,1-dimethyl-indan-5-ol

To a solution of 6-fluoro-5-methoxy-1,1-dimethyl-indan (1.40 g, 7.21 mmol) in 20.0 ml of DCM at −78° C. was added BBr$_3$ (1.40 ml, 14.4 mmol) in DCM (10.0 ml). The reaction mixture was stirred at −78° C. for two hours before being treated with 2.0 ml of methanol. This mixture was stirred for few minutes after which a saturated solution of NaHCO$_3$ was carefully added and the resulting mixture stirred for an additional 1 hour. The mixture was extracted with DCM (3×40 mL) and the combined organic extracts were washed with brine and dried over Na$_2$SO$_4$. Flash column chromatography on silica gel (2-10% ethyl acetate/heptanes) afforded 0.985 g of the title compound.

$C_{11}H_{13}FO$, (180.09), MS (EI$^+$): 108.08 (M$^+$)
$^1$H NMR (300 MHz, CDCl$_3$): δ 6.81 (m, 2H), 4.89 (d, 1H), 2.80 (m, 2H), 1.91 (m, 2H), 1.22 (s, 6H)

Step 3: (S)-2-(6-Fluoro-1,1-dimethyl-indan-5-yloxymethyl)-2,3-dihydro-oxazolo[3,2-a]pyrimidin-7-one To a solution of toluene-4-sulfonic acid (S)-7-oxo-2,3-dihydro-7H-oxazolo[3,2-a]pyrimidin-2-ylmethyl ester (prepared in accordance with the procedures described in WO 2008/112483) (0.927 g, 2.88 mmol) in acetonitrile (40 ml) was added 6-fluoro-1,1-dimethyl-indan-5-ol (0.570 g, 3.16 mmol) followed by cesium carbonate (0.937 g, 2.88 mmol). The reaction mixture was heated at reflux for 1 hour and allowed to cool to room temperature. The reaction mixture was concentrated and the residue treated with water (60 ml) and extracted with ethyl acetate (100 ml). The organic layer was washed with brine, dried over Na$_2$SO$_4$, filtered, and concentrated. Flash chromatography (silica gel, 0-5% MeOH/CH$_2$Cl$_2$) afforded 0.295 g of the title compound as a white solid. $[\alpha]_D^{25}$=−17.8 (c=0.65, CHCl$_3$).

$C_{18}H_{19}FN_2O_3$, (330.14), LCMS (ESI): 331.14 (M$^+$+H)
$^1$H NMR (300 MHz, CDCl$_3$): δ 7.23 (d, 1H), 6.82 (m, 2H), 6.08 (d, 1H), 5.23 (m, 1H), 4.40-4.26 (m, 4H), 2.83 (m, 2H), 1.93 (m, 2H), 1.22 (s, 6H)

Example 12

(S)-2-(1,1-Dimethyl-indan-5-yloxymethyl)-5-methyl-2,3-dihydro-oxazolo[3,2-a]pyrimidin-7-one

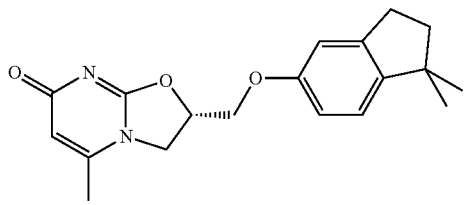 [SMILES: Cc1cc(=O)nc2n1C[C@@H](COc1ccc3c(c1)CCC3(C)C)O2]

Step 1: Toluene-4-sulfonic acid (S)-2-amino-4,5-dihydro-oxazolo-5-ylmethyl ester To a suspension of sodium hydrogen cyanamide (7.16 g, 112 mmol) in methanol (100 ml) was added a solution of (2S)-(+)-glycidyl tosylate (25 g, 110 mmol) in methanol (100 ml) dropwise over 30 minutes at room temperature. The mixture was stirred at room temperature for 18 hours. The mixture was concentrated and the residue treated with water (100 ml) and extracted with ethyl acetate (200 ml). The organic layer was washed twice with water, dried over magnesium sulfate and filtered. The concentrated filtrate was treated with 10% ethyl acetate/heptane. The precipitate which formed was collected to give the title compound as a solid, 108-112° C. mp (8.0 g, 27%).

$C_{11}H_{14}N_2O_4S$, (270.07), LCMS (ESI): 271.06 (M$^+$+H)

Step 2: Toluene-4-sulfonic acid (S)-5-methyl-7-oxo-2,3-dihydro-7H-oxazolo[3,2-a]pyrimidin-2-ylmethyl ester A stirred mixture of toluene-4-sulfonic acid (S)-2-amino-4,5-dihydro-oxazolo-5-ylmethyl ester (2.7 g, 10 mmol) and ethyl 2-butynoate (1.12 g, 10 mmol) in 20 ml of ethanol was heated at reflux for 4 hours. The solution was concentrated and the residue was purified by flash chromatography on silica gel using 0-10% methanol/methylene chloride to give the title compound as a tacky solid (1.0 g, 30%)

$C_{15}H_{16}N_2O_5S$, (336.08), LCMS (ESI): 337.07 (M$^+$+H)

Step 3: (S)-2-(1,1-Dimethyl-indan-5-yloxymethyl)-5-methyl-2,3-dihydro-oxazolo[3,2-a]pyrimidin-7-one To a solution of toluene-4-sulfonic acid (S)-5-methyl-7-oxo-2,3-dihydro-7H-oxazolo[3,2-a]pyrimidin-2-ylmethyl ester (0.300 g, 0.892 mmol) in acetonitrile (20 ml) was added 1,1-dimethyl-indan-5-ol (0.145 g, 0.892 mmol) (see Example 1) followed by cesium carbonate (0.290 g, 0.892 mmol). The reaction mixture was heated at reflux for 1 hour, then allowed to cool to room temperature. The solvent was removed under vacuum. The residue was treated with water (20 ml) and extracted with ethyl acetate (50 ml). The organic layer was washed with brine, dried over Na$_2$SO$_4$, filtered, and concentrated. Purification via flash column chromatography (silica gel, 0-5% MeOH/CH$_2$Cl$_2$) afforded 0.045 g of the title compound as a white solid. $[\alpha]_D^{25}$=−38.7 (c=0.68, CHCl$_3$).

$C_{19}H_{22}N_2O_3$, (326.16), LCMS (ESI): 327.17 (M$^+$+H)
$^1$H NMR (300 MHz, CDCl$_3$): δ 7.03 (d, 1H), 6.71 (m, 2H), 5.84 (s, 1H), 5.24 (m, 1H), 4.45-4.19 (m, 4H), 2.84 (t, 2H), 2.24 (s, 3H), 1.92 (t, 2H), 1.23 (s, 6H)

Example 13

(S)-2-(6-Chloro-1,1-dimethyl-indan-5-yloxymethyl)-2,3-dihydro-oxazolo[3,2-a]pyrimidin-7-one

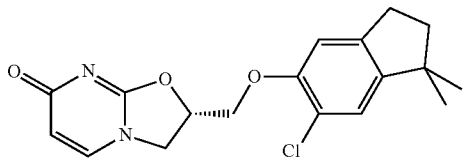 [SMILES: CC1(C)CCc2cc(OC[C@@H]3Cn4ccc(=O)nc4O3)c(Cl)cc21]

Step 1: 6-Chloro-5-methoxy-1,1-dimethyl-indan

To a solution of 6-bromo-5-methoxy-1,1-dimethyl-indan (2.00 g, 7.84 mmol) in THF (30 mL) at −78° C. was slowly added n-butyllithium (4.0 mL, 2.5 M in hexane). The resulting solution was stirred at −78° C. for 0.5 h and a solution of N-chlorosuccinimide (1.26 g, 9.40 mmol) in THF (30 mL) was added. After an additional 2 h at −78° C., the reaction was warmed to room temperature, poured into water (50 mL) and extracted with ethyl acetate (2×70 mL). The combined organic layers were washed with water, brine, dried over sodium sulfate, filtered, and concentrated. Purification by silica gel chromatography (2% ethyl acetate/heptane) afforded the title compound as a yellow oil.

$C_{12}H_{15}ClO$, (210.08), MS (EI$^+$): 210.06 (M$^+$)

Step 2: 6-Chloro-1,1-dimethyl-indan-5-ol

The title compound was prepared from 6-chloro-5-methoxy-1,1-dimethyl-indan by treatment with BBr$_3$ as in Example 11.

$C_{11}H_{13}ClO$, (196.06), LCMS (ESI$^-$): 195.05 (M−H)
$^1$H NMR (300 MHz, CDCl$_3$): δ 7.07 (s, 1H), 6.88 (s, 1H), 5.47 (s, 1H), 2.86 (t, 2H), 1.95 (t, 2H), 1.25 (s, 6H).

Step 3: (S)-2-(6-Chloro-1,1-dimethyl-indan-5-yloxymethyl)-2,3-dihydro-oxazolo[3,2-a]pyrimidin-7-one To a solution of toluene-4-sulfonic acid (S)-7-oxo-2,3-dihydro-7H-oxazolo[3,2-a]pyrimidin-2-ylmethyl ester (see Example 1, (0.393 g, 1.22 mmol) in acetonitrile (150 ml) was added 6-chloro-1,1-dimethyl-indan-5-ol (0.240 g, 1.220 mmol) followed by cesium carbonate (0.397 g, 1.22 mmol). The reaction mixture was heated at reflux for 1.5 hour, after which it was allowed to cool to room temperature. The solvent from the reaction mixture was removed under vacuum. The residue was treated with water (100 ml) and extracted with dichloromethane (2×150 mL). The organic layer was washed with brine (300 mL), dried over Na$_2$SO$_4$, filtered, and concentrated. Purification via flash column chromatography (silica gel, 1-5% 7N NH$_3$ in MeOH/CH$_2$Cl$_2$) afforded 0.180 g of the title compound as a white solid.

$C_{18}H_{19}ClN_2O_3$, (346.11), LCMS (ESI): 347.12 (M$^+$+H)
$^1$H NMR (300 MHz, CDCl$_3$): δ 7.31 (d, 1H), 7.03 (s, 1H), 6.79 (s, 1H), 5.96 (d, 1H), 5.34 (m, 1H), 4.55-4.17 (m, 4H), 2.82 (t, 2H), 1.91 (t, 2H), 1.19 (s, 6H)

Comparative Example 1

(S)-2-(Indan-5-yloxymethyl)-2,3-dihydro-oxazolo[3,2-a]pyrimidin-7-one

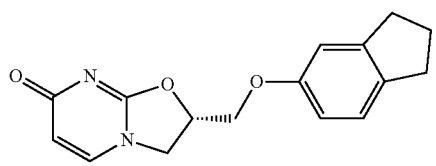 [SMILES: O=c1ccn2c(n1)O[C@H](COc1ccc3c(c1)CCC3)C2]

To a solution of (S)-2-toluene-4-sulfonic acid methyl-2,3-dihydro-oxazolo[3,2-a]pyrimidin-7-one (0.80 g, 2.48 mmol) (prepared in accordance with the procedures described in WO 2008/112483) in acetonitrile (80 ml) was added indan-5-ol (0.33 g, 2.48 mmol), followed by addition of cesium carbonate (0.82 g, 2.48 mmol). The reaction mixture was stirred at reflux for 1 hour. It was then concentrated and the residue was dissolved in ethyl acetate/water. The whole was extracted with ethyl acetate. The organic phase was washed with 3 percent HCl, saturated NaHCO$_3$, brine, and dried (Na$_2$SO$_4$). Silica gel chromatography (silica, 7N NH$_3$ in methanol/methylene chloride) provided 0.33 g (47%) of the title compound. [α]$_D^{25}$=−62.9, (c=0.94, CHCl$_3$)

$C_{16}H_{16}N_2O_3$ (284.12), LCMS (ES$^+$): 285.14 (M$^+$+H).

$^1$H NMR (CDCl$_3$, 300 MHz), δ 7.24 (d, 1H), 7.12 (d, 1H), 6.76 (s, 1H), 6.65 (dd, 1H), 6.09 (d, 1H), 5.26 (m, 1H), 4.19~4.41 (m, 4H), 2.85 (q, 4H), 2.08 (qn, 2H).

Comparative Example 2

(S)-2-(5,6,7,8-Tetrahydro-naphthalen-2-yloxymethyl)-2,3-dihydro-oxazolo[3,2-a]pyrimidin-7-one

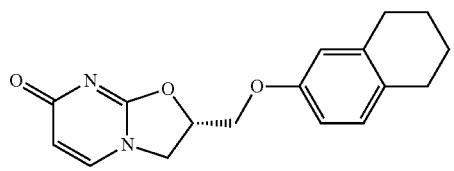 [SMILES: O=c1ccn2c(n1)O[C@H](COc1ccc3c(c1)CCCC3)C2]

The title compound was prepared from 5,6,7,8-tetrahydro-naphthalen-2-ol employing the procedure described in Comparative Example 1. [α]$_D^{25}$=−59.6 (c=0.95, CHCl$_3$).

$C_{17}H_{18}N_2O_3$ (298.13), LCMS (ESI): 299.15 (M$^+$+H).
$^1$H NMR (CDCl$_3$, 300 MHz), δ 7.24 (d, 1H), 6.98 (d, 1H), 6.62 (dd, 1H), 6.58 (s, 1H), 6.08 (d, 1H), 5.25 (m, 1H), 4.18~4.40 (m, 4H), 2.71 (m, 4H), 1.77 (m, 4H).

Comparative Example 3

(R)-2-(1,1-Dimethyl-indan-5-yloxymethyl)-2,3-dihydro-oxazolo[3,2-a]pyrimidin-7-one

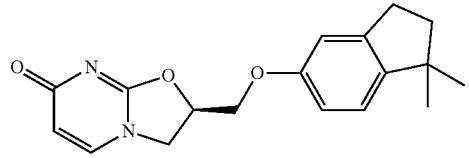 [SMILES: CC1(C)CCc2cc(OC[C@H]3Cn4ccc(=O)nc4O3)ccc21]

The title compound was prepared from 1,1-dimethyl-indan-5-ol and (R)-2-toluene-4-sulfonic acid methyl-2,3-dihydro-oxazolo[3,2-a]pyrimidin-7-one employing the procedure described in Example 1. [α]$_D^{25}$=−53.8 (c=1.12, CHCl$_3$).

$C_{18}H_{20}N_2O_3$ (312.14), LCMS (ES$^+$): 313.16 (M$^+$+H).
$^1$H NMR (CDCl$_3$, 300 MHz), δ 7.24 (d, 1H), 7.03 (d, 1H), 6.71 (s, 1H), 6.69 (d, 1H), 6.09 (d, 1H), 5.26 (m, 1H), 4.20~4.40 (m, 4H), 2.85 (t, 2H), 1.92 (t, 2H), 1.22 (s, 6H).

Biological Examples

Example 14

A calcium ion (Ca$^2$) mobilization assay was used to identify and determine the activity for allosteric modulators of the rat or human mGluR2 receptor. Two formats were used: (1) examine the ability of glutamate to affect the potency of the modulator, by looking at a concentration-response curve of compound at different submaximal glutamate concentrations, and (2) look at the ability of the modulator to affect the potency of glutamate by looking at a concentration-response curve of glutamate at a maximal modulator concentration.

To monitor functional receptor response using calcium mobilization, a cell line stably expressing the rat or human mGluR2 receptor (normally coupled to its intracellular effector molecules through an inhibitory G-protein, Gαi) and Gα₁₆, in a tetracycline-inducible vector was created. Gα16 can promiscuously couple Gs and Gi-coupled receptors to the inositol phospholipid signaling pathway by activating phospholipase Cβ resulting in a $Ca^{2+}$ signal (normally Gαq-mediated), that can be monitored with fluorescence plate readers such as FLIPR (Molecular Devices, Fluorescence Imaging Plate Reader), FDSS6000 (Hamamatsu, Fluorescence Drug Screening System), or FlexStation (Molecular Devices). The $Ca^{2+}$ mobilization assay was based on the detection of intracellular calcium changes using a selective, calcium-chelating dye: Fluo-3, Fluo-4, or Calcium-3. A large fluorescence intensity increase was observed upon calcium association with the dye. The dye was delivered either with the acetoxymethyl ester, and washed off, or using a no-wash kit (Molecular Devices). Fluorescence signals stimulated by glutamate were recorded and used to generate the following pharmacological parameters: (1) the potency (EC50) of the compound(s) of interest at approx. EC 10 for glutamate at the rat and human mGluR2 receptors respectively, and (2) a fold-shift of the glutamate EC50 by maximal concentration of compound(s) of interest.

Generally the compounds of this invention exhibit good mGluR2 potentiation (EC50). Broadly speaking the activity of the compounds of this invention is in the range of about 1-1000 nM, and certain of the compounds exhibit mGluR2 potentiation in the range of 1-100 nM. The results obtained for a few of the representative compounds of formula (I) of this invention tested in accordance with this procedure are summarized in Table 1, which lists the mGluR2 potentiation (EC50).

TABLE I

| Example | mGluR2 Potentiation (nM) |
|---|---|
| 1 | 29 |
| 2 | 19 |
| 3 | 11 |
| 4 | 15 |
| 7 | 20 |
| 8 | 17 |
| 9 | 64 |
| 10 | 15 |
| Comparative Ex. 1 | 445 |
| Comparative Ex. 2 | 224 |
| Comparative Ex. 3 | 9100 |

The efficacy of the compounds of formula (I) of this invention in treating a variety of diseases as disclosed herein can be confirmed by any of the methods known to one skilled in the art. For instance, the efficacy in treating anxiety can be confirmed by using Vogel conflict test. See, for example, Tatarczynska et al., Psychopharmacology (Berl). 2001 October; 158(1):94-9 incorporated herein by reference in its entirety. Specifically, Tatarczynska et al. disclose the antianxiety-like effects of antagonists of group I and agonists of group II and III metabotropic glutamate receptors.

The preclinical anxiety and psychosis models also include stress induced hyperthermia, fear potentiated startle and PCP-induced hyperlocomotion. See Rorick-Kehn et al., J. Pharmacol. Exp. Ther. 2006 February; 316(2):905-13. Epub 2005 Oct. 13. Also see, Johnson et al., Psychopharmacology (Berl). 2005 April; 179(1):271-83. Epub 2005 Feb. 17. Fear-potentiated startle and elevated plus maze models have been used by Helton et al., J Pharmacol Exp Ther. 1998 February; 284(2):651-660 in order to demonstrate the anxiolytic and side-effect profile of LY354740: a potent, highly selective, orally active agonist for group II metabotropic glutamate receptors.

Various anxiety models to show efficacy in humans are also known in the art. See Kellner et al., Psychopharmacology (Berl). 2005 April; 179(1):310-5. Epub 2004 Sep. 30, where the effects of a metabotropic glutamate(2/3) receptor agonist on panic anxiety induced by cholecystokinin tetrapeptide in healthy humans has been reported.

In addition, the efficacy of the compounds of formula (I) of this invention in treating schizophrenia may also be ascertained by various known models in the art. For instance, PCP-induced hyperlocomotion, PCP-disrupted prepulse inhibition, stress-induced hyperthermia, and elevated plus maze models have been used to demonstrate the efficacy of allosteric modulators of mGluR2. See, Galici et al., J Pharmacol Exp Ther. 2006 July; 318(1):173-85. Epub 2006 Apr. 11, where it is shown that biphenyl-indanone A, a positive allosteric modulator of the mGluR2, has antipsychotic- and anxiolytic-like effects in mice.

The efficacy of the compounds of formula (I) of this invention in improving the working memory in humans can be ascertained by a variety of methods known in the art. For instance, Krystal et al., Psychopharmacology (Berl). 2005 April; 179(1):303-9. Epub 2004 Aug. 10, reported that the attenuation of the disruptive effects of the NMDA glutamate receptor antagonist, ketamine, on working memory by pretreatment with the group II metabotropic glutamate receptor agonist, LY354740, in healthy human subjects. In another example, Patil et al., Nature Medicine. 2007 September; 13(9):1102-7. Epub 2007 Sep. 2. reported that the group II metabotropic glutamate receptor agonist, LY2140023, showed statistically significant improvements in both positive and negative symptoms of schizophrenia compared to placebo.

The compounds of formula (I) of this invention are also useful in treating sleep disorders and depression. Feinberg et al., Pharmacol Biochem Behav. 2002, 73(2) 467-74, have reported that the selective group mGluR2/3 receptor agonist, LY379268, suppresses rapid eye movement (REM) sleep and fast EEG in the rat. Gewirtz et al., Pharmacol Biochem Behav. 2002 September; 73(2):317-26, have examined the effects of mGluR2/3 agonists on BDNF mRNA expression in medial prefrontal cortex induced by the hallucinogen and $5HT_{2A/2B/2C}$ agonist. Also, see Schechter et al., NeuroRx. 2005 October; 2(4):590-611. Review, where innovative approaches for the development of antidepressant drugs are reviewed.

The activity of allosteric modulators of mGluR2 in pain models has also been reported in the literature. See, Jones et al., Neuropharmacology. 2005; 49 Suppl 1:206-18, where analgesic effects of the selective group II (mGlu2/3) metabotropic glutamate receptor agonists are disclosed.

The efficacy of compounds of formula (I) of this invention in treating epilepsy can also be ascertained by various methods used in the art. For example, see, Alexander et al., Epilepsy Res. 2006, 71(1), 1-22, where metabotropic glutamate receptors as a strategic target for the treatment of epilepsy is discussed. Also see, Klodzinska et al., Pol J. Pharmacol. 1999, 51(6), 543-5, which discloses selective group II glutamate metabotropic receptor agonist LY354740 attenuates pentylenetetrazole- and picrotoxin-induced seizures. Roles of metabotropic glutamate receptor subtypes in modulation of pentylenetetrazole-induced seizure activity in mice is disclosed by Thomsen et al., Neuropharmacology. 1998, 37(12), 1465-73. Finally, Thomsen et al., J. Neurochem. 1994, 62(6), 2492-5, disclose that (S)-4-carboxy-3-hydroxyphenylglycine, an antagonist of metabotropic glutamate receptor (mGluR) 1a and an agonist of mGluR2, protects against audiogenic seizures in DBA/2 mice.

It has also been reported in the literature that modulation mGluR2 receptors may also improve cognitive functions. See for example Moghaddam, Psychopharmacology (2004) 174: 39-44. Accordingly, it has been further suggested that modulation of mGluR2 receptors may also improve cognitive deficits in patients suffering from either Parkinson's disease as well as Alzheimer's disease. See specifically Lee et al., Brain Research 1249 (2009), 244-250 for Alzheimer's disease and Samadi et al., Neuropharmacology 54 (2008) 258-268 for Parkinson's disease.

Example 15

Stress Induced Hyperthermia (Anxiety Model)

Stress-induced hyperthermia (SIH) reflects the elevation in core body temperature experienced by mammals following a stressful experience. Clinically active anxiolytics prevent SIH, indicating that this model may be useful in identifying novel anxiolytic agents (See, Olivier et al. Eur J. Pharmacol. 2003, 463, 117-32). SIH is measured in mice using the rectal test procedure adaptation of the classic SIH paradigm described by Borsini et al, Psychopharmacology (Berl). 1989, 98(2), 207-11. Individually housed mice are subjected to two sequential rectal temperature measurements, separated by a 10-minute interval. The first measurement captured the animal's basal core body temperature (T1), while the second temperature (T2) captured body temperature following the mild stress imposed by the first temperature measurement. The difference between the first and second temperature (T2-T1 or ΔT) is the SIH. Temperature measurements are made to the nearest 0.1° C. with a lubricated thermistor probe inserted 2 cm into the rectum of each subject. Test compounds are administered 60 minutes before the first temperature measurement to allow for any stress effect created by the injection to dissipate completely.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of the formula (I):

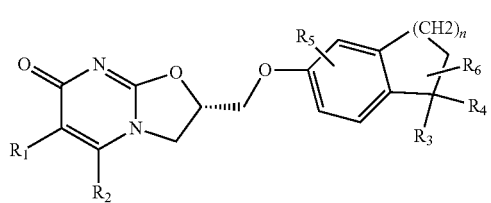

wherein:
n is 1, 2 or 3;
$R_1$ is selected from the group consisting of hydrogen, methyl, fluoromethyl, ethyl, 2-fluoroethyl and propyl;
$R_2$ is selected from the group consisting of hydrogen, methyl, fluoromethyl, ethyl, 2-fluoroethyl, propyl, 1,1-difluoropropyl, methoxymethyl and 2-fluoroethoxymethyl;
$R_3$ and $R_4$ are the same or different and independently of each other selected from the group consisting of ($C_1$-$C_4$) alkyl, phenyl and benzyl; and
$R_5$ and $R_6$ are the same or different and independently of each other selected from the group consisting of hydrogen, halogen, ($C_1$-$C_4$)alkyl and ($C_1$-$C_4$)alkoxy.

2. The compound according to claim 1, which has the formula II:

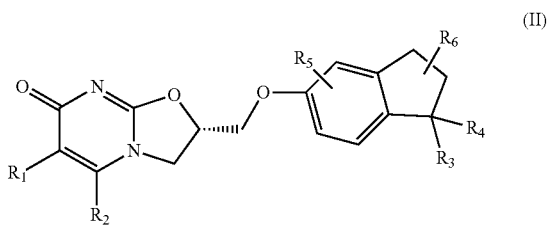

wherein:
$R_1$ is selected from the group consisting of hydrogen, methyl and ethyl;
$R_2$ is selected from the group consisting of hydrogen, methyl, ethyl, propyl and 1,1-difluoropropyl;
$R_3$ and $R_4$ are the same or different and independently of each other selected from the group consisting of methyl, ethyl and propyl; and
$R_5$ and $R_6$ are the same or different and independently of each other selected from the group consisting of hydrogen, fluorine, bromine, methyl and ethyl.

3. The compound according to claim 2, wherein:
$R_1$ is hydrogen or ethyl;
$R_2$ is hydrogen or methyl;
$R_3$ and $R_4$ are each methyl; and
$R_5$ is hydrogen or methyl;
$R_6$ is hydrogen or methyl.

4. The compound according to claim 2, which is selected from the group consisting of:
(S)-2-(1,1-dimethyl-indan-5-yloxymethyl)-2,3-dihydro-oxazolo[3,2-a]pyrimidin-7-one;
(S)-2-(6-bromo-1,1-dimethyl-indan-5-yloxymethyl)-2,3-dihydro-oxazolo[3,2-a]pyrimidin-7-one;
(S)-2-(6-chloro-1,1-dimethyl-indan-5-yloxymethyl)-2,3-dihydro-oxazolo[3,2-a]pyrimidin-7-one;
(S)-2-(6-fluoro-1,1-dimethyl-indan-5-yloxymethyl)-2,3-dihydro-oxazolo[3,2-a]pyrimidin-7-one;
(S)-2-(1,1,6-trimethyl-indan-5-yloxymethyl)-2,3-dihydro-oxazolo[3,2-a]pyrimidin-7-one;
(S)-2-(1,1-dimethyl-indan-5-yloxymethyl)-6-ethyl-2,3-dihydro-oxazolo[3,2-a]pyrimidin-7-one;
(S)-5-(1,1-difluoro-propyl)-2-(1,1-dimethyl-indan-5-yloxymethyl)-2,3-dihydro-oxazolo[3,2-a]pyrimidin-7-one; and
(S)-2-(1,1-dimethyl-indan-5-yloxymethyl)-5-methyl-2,3-dihydro-oxazolo[3,2-a]pyrimidin-7-one.

5. The compound according to claim 2, which is selected from the group consisting of:
(S)-2-(6-fluoro-1,1-dimethyl-indan-5-yloxymethyl)-2,3-dihydro-oxazolo[3,2-a]pyrimidin-7-one;
(S)-2-(6-bromo-1,1-dimethyl-indan-5-yloxymethyl)-2,3-dihydro-oxazolo[3,2-a]pyrimidin-7-one;
(S)-2-(1,1,6-trimethyl-indan-5-yloxymethyl)-2,3-dihydro-oxazolo[3,2-a]pyrimidin-7-one; and
(S)-2-(6-chloro-1,1-dimethyl-indan-5-yloxymethyl)-2,3-dihydro-oxazolo[3,2-a]pyrimidin-7-one.

6. The compound according to claim 1, which has the formula III:

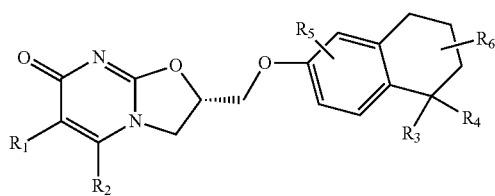

(III)

wherein:
R₁ is selected from the group consisting of hydrogen, methyl and ethyl;
R₂ is selected from the group consisting of hydrogen, methyl, ethyl, propyl and 1,1-difluoropropyl;
R₃ and R₄ are the same or different and independently of each other selected from the group consisting of methyl, ethyl and propyl; and
R₅ and R₆ are the same or different and independently of each other selected from the group consisting of hydrogen, fluorine, chlorine, bromine, methyl and ethyl.

7. The compound according to claim 6, wherein:
R₁ is hydrogen or ethyl;
R₂ is hydrogen, methyl or 1,1-difluoropropyl;
R₃ and R₄ are each methyl; and
R₅ is hydrogen, fluorine, or methyl;
R₆ is hydrogen or methyl.

8. A compound selected from the group consisting of:
(S)-2-(5,5-dimethyl-5,6,7,8-tetrahydro-naphthalen-2-yloxymethyl)-2,3-dihydro-oxazolo[3,2-a]pyrimidin-7-one;
(S)-2-(5,5-dimethyl-5,6,7,8-tetrahydro-naphthalen-2-yloxymethyl)-6-ethyl-2,3-dihydro-oxazolo[3,2-a]pyrimidin-7-one
(S)-2-(5,5,8,8-tetramethyl-5,6,7,8-tetrahydro-naphthalen-2-yloxymethyl)-2,3-dihydro-oxazolo[3,2-a]pyrimidin-7-one; and
(S)-5-(1,1-difluoro-propyl)-2-(5,5-dimethyl-5,6,7,8-tetrahydro-naphthalen-2-yloxymethyl)-2,3-dihydro-oxazolo[3,2-a]pyrimidin-7-one.

9. A compound of the formula IV:

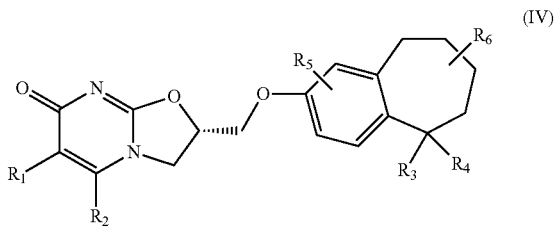

(IV)

wherein:
R₁ is selected from the group consisting of hydrogen, methyl and ethyl;
R₂ is selected from the group consisting of hydrogen, methyl, ethyl, propyl and 1,1-difluoropropyl;
R₃ and R₄ are the same or different and independently of each other selected from the group consisting of methyl, ethyl and propyl; and
R₅ and R₆ are the same or different and independently of each other selected from the group consisting of hydrogen, fluorine, chlorine, bromine, methyl and ethyl.

10. The compound according to claim 9, wherein:
R₁ is hydrogen;
R₂ is hydrogen;
R₃ and R₄ are each methyl; and
R₅ is hydrogen, fluorine or methyl;
R₆ is hydrogen or methyl.

11. The compound according to claim 9, which is:
(S)-2-(5,5-dimethyl-6,7,8,9-tetrahydro-5H-benzocyclohepten-2-yloxymethyl)-2,3-dihydro-oxazolo[3,2-a]pyrimidin-7-one.

12. A pharmaceutical composition comprising one or more compounds according to any one of claims 1 to 11 in combination with one or more pharmaceutically acceptable carriers, diluents or excipients.

* * * * *